(12) United States Patent
Zhou et al.

(10) Patent No.: US 11,593,560 B2
(45) Date of Patent: Feb. 28, 2023

(54) SYSTEM AND METHOD FOR RELATION EXTRACTION WITH ADAPTIVE THRESHOLDING AND LOCALIZED CONTEXT POOLING

(71) Applicants: Beijing Wodong Tianjun Information Technology Co., Ltd., Beijing (CN); JD.com American Technologies Corporation, Mountain View, CA (US)

(72) Inventors: Wenxuan Zhou, Los Angeles, CA (US); Kevin Huang, Sunnyvale, CA (US); Jing Huang, Mountain View, CA (US)

(73) Assignees: Beijing Wodong Tianjun Information Technology Co., Ltd., Beijing (CN); JD.com American Technologies Corporation, Mountain View, CA (US)

( * ) Notice: Subject to any disclaimer, the term of this patent is extended or adjusted under 35 U.S.C. 154(b) by 339 days.

(21) Appl. No.: 17/076,014

(22) Filed: Oct. 21, 2020

(65) Prior Publication Data
US 2022/0121822 A1 Apr. 21, 2022

(51) Int. Cl.
*G06F 40/295* (2020.01)
*G06F 16/93* (2019.01)
(Continued)

(52) U.S. Cl.
CPC ............ *G06F 40/295* (2020.01); *G06F 16/93* (2019.01); *G06N 20/00* (2019.01); *G06Q 10/10* (2013.01); *G16H 70/60* (2018.01)

(58) Field of Classification Search
CPC ....... G06F 40/295; G06F 16/93; G06N 20/00; G15H 70/60
See application file for complete search history.

(56) References Cited

U.S. PATENT DOCUMENTS 9,886,948 B1 * 2/2018 Garimella ............... G10L 15/16
10,332,509 B2 * 6/2019 Catanzaro ............... G10L 15/02
(Continued)

FOREIGN PATENT DOCUMENTS

CN 107273349 A 10/2017
CN 110059320 A 7/2019

OTHER PUBLICATIONS

Yuhao Zhang, Victor Zhong, Danqi Chen, Gabor Angeli, and Christopher D. Manning, Position-aware attention and supervised data improve slot filling, EMNLP, 2017, 35-45.
(Continued)

*Primary Examiner* — Akwasi M Sarpong
(74) *Attorney, Agent, or Firm* — Scully, Scott, Murphy & Presser, P.C.

(57) ABSTRACT

System and method for relation extraction using adaptive thresholding and localized context pooling (ATLOP). The system includes a computing device, the computing device has a processor and a storage device storing computer executable code. The computer executable code is configured to provide a document; embed entities in the document into embedding vectors; and predict relations between a pair of entities in the document using their embedding vectors. The relation prediction is performed based on an improved language model. Each relation has an adaptive threshold, and the relation between the pair of entities is determined to exist when a logit of the relation between the pair of entities is greater than a logit function of the corresponding adaptive threshold.

18 Claims, 9 Drawing Sheets

*John Stanistreet* was an *Australian* politician. He was born in *Bendigo* to legal manager *John Jepson Stanistreet and Maud McIlroy.* (...4 sentences...) In 1955 *John Stanistreet* was elected to the *Victorian Legislative Assembly* as the *Liberal and Country Party* member for *Bendigo. Stanistreet* died in *Bendigo* in 1971.

Subject: John Stanistreet    Object: Bendigo

Relation: place of birth; place of death

(51) Int. Cl.
   *G06N 20/00* (2019.01)
   *G16H 70/60* (2018.01)
   *G06Q 10/10* (2012.01)

(56) References Cited

U.S. PATENT DOCUMENTS

| | | | | |
|---|---|---|---|---|
| 2016/0284347 | A1* | 9/2016 | Sainath | G06N 3/084 |
| 2017/0278514 | A1* | 9/2017 | Mathias | G10L 15/26 |
| 2018/0373789 | A1 | 12/2018 | Ho et al. | |
| 2019/0197104 | A1 | 6/2019 | Fauceglia et al. | |
| 2019/0244611 | A1* | 8/2019 | Godambe | G10L 15/22 |
| 2020/0160846 | A1* | 5/2020 | Itakura | G10L 15/14 |
| 2022/0246149 | A1* | 8/2022 | Kumar | G06N 5/022 |

OTHER PUBLICATIONS

Zhengyan Zhang, Xu Han, Zhiyuan Liu, Xin Jiang, Maosong Sun, and Qun Liu, ERNIE: enhanced language representation with informative entities, 2019, arXiv:1905.07129.

Heliang Zheng, Jianlong Fu, Zheng-Jun Zha, and Jiebo Luo, Learning deep bilinear transformation for fine-grained image representation, 2019, arXiv:1911.03621.

PCT/CN2021/121006, International Search Report and the Written Opinion, dated Dec. 29, 2021.

Christoph Alt, Marc Hubner, and Leonhard Hennig, Improving relation extraction by pre-trained language representations, 2019, arXiv:1906.03088.

Iz Beltagy, Kyle Lo, and Arman Cohan, SciBERT: a pretrained language model for scientific text, 2019, arXiv:1903.10676.

Fenia Christopoulou, Makoto Miwa, and Sophia Ananiadou, A walk-based model on entity graphs for relation extraction, 2018, arXiv:1902.07023.

Fenia Christopoulou, Makoto Miwa, and Sophia Ananiadou, Connecting the dots: document-level neural relation extraction with edge-oriented graphs, 2019, arXiv:1909.00228.

Junyong Chung, Caglar Gulcehre, KyungHyun Cho, and Yoshua Bengio, Empirical evaluation of gated recurrent neural networks on sequence modeling, 2014, arXiv:1412.3555.

Kevin Clark, Urvashi Khandelwal, Omer Levy, Christopher D. Manning, What does BERT look at? An analysis of BERT'S attention, 2019, arXiv:1906.04341.

Jacob Devlin, Ming-Wei Chang, Kenton Lee, Kristina Toutanova, BERT: pre-training of deep bidirectional transformers for language understanding, 2019, arXiv:1810.04805.

Rong-En Fan, and Chih-Jen Lin, A study on threshold selection for multi-label classification, 2007, Semantic Scholar.

Priya Goyal, Piotr Dollár, Ross Girshick, Pieter Noordhuis, Lukasz Wesolowski, Aapo Kyrola, Andrew Tulloch, Yangqing Jia, Kaiming He, Accurate, large minibatch SGD: training ImageNet in 1 hour, 2017, arXiv:1706.02677.

Zhijiang Guo, Yan Zhang, and Wei Lu, Attention guided graph convolutional networks for relation extraction, 2019, Proceedings of the 57th Annual Meeting of the Association for Computational Linguistics, 241-251.

Pankaj Gupta, Subburam Rajaram, Hinrich Schutze, Bernt Andrassy, Thomas Runkler, Neural relation extraction within and across sentence boundaries, 2019, arXiv:1810.05102.

Iris Hendrickx, Su Nam Kim, Zornitsa Kozareva, Preslav Nakov, Diarmuid Ó Séaghdha, Sebastian Padó, Marco Pennacchiotti, Lorenza Romano, Stan Szpakowicz, SemEval-2010 Task 8: multi-way classification of semantic relations between pairs of nominals, 2010, Proceedings of the 5th International Workshop on Semantic Evaluation, 33-38.

John Hewitt, Christopher D. Manning, A structural probe for finding syntax in word representations, NAACL-HLT, 2019, 4129-4138.

Sepp Hochreiter and Jurgen Schmidhuber, Long short-term memory. Neural Computation, 1997, 9(8): 1735-1780.

Robin Jia, Cliff Wong, and Hoifung Poon, Document-level N-ary relation extraction with multiscale representation learning, 2019, arXiv:1904.02347.

Urvashi Khandelwal, He He, Peng Qi, and Dan Jurafsky, Sharp nearby, fuzzy far away: how neural language models use context, 2018, arXiv:1805.04623.

Thomas N. Kipf and Max Welling, Semi-supervised classification with graph convolutional networks, 2017, arXiv:1609.02907.

Jiao Li, Yueping Sun, Robin J. Johnson, Daniela Sciaky, Chih-Hsuan Wei, Robert Leaman, Allan Peter Davis, Carolyn J. Mattingly, Thomas C. Wiegers, and Zhiyong Lu, BioCreative V CDR task corpus: a resource for chemical disease relation extraction, Database, 2016, 1-10.

Yann LeCun, Yoshua Bengio & Geoffrey Hinton, Deep learning, Nature, 2015, 521:436-444.

Xiaodan Liang, Xiaohui Shen, Jiashi Feng, Liang Lin, and Shuicheng Yan, Semantic object parsing with graph LSTM, 2016, arXiv:1603.07063.

Yang Liu, and Mirella Lapata, Learning structured text representations, Transactions of the Association for Computational Linguistics, 2018, 6: 63-75.

Yinhan Liu, Myle Ott, Naman Goyal, Jingfei Du, Mandar Joshi, Danqi Chen, Omer Levy, Mike Lewis, Luke Zettlemoyer, Veselin Stoyanov, RoBERTa: a robustly optimized BERT pretraining approach, 2019, arXiv:1907.11692.

Ilya Loshchilov, and Frank Hutter, Decoupled weight decay regularization, 2019, ICLR 2019 Conference.

Aditya K. Menon, Ankit Singh Rawat, Sashank Reddi, and Sanjiv Kumar, Multilabel reductions: what is my loss optimising? 2019, NeurIPS2019.

Paulius Micikevicius, Sharan Narang, Jonah Alben, Gregory Diamos, Erich Eisen, David Garcia, Boris Ginsburg, Michael Houston, Oleksii Kuchaiev, Ganesh Venkatesh, Hao Wu, Mixed precision training, 2018, arXiv:1710.03740.

Makoto Miwa, Mohit Bansal, End-to-End Relation Extraction using LSTMs on sequences and tree structures, 2016, arXiv:1601.00770.

Guoshun Nan, Zhijiang Guo, Ivan Sekulic, Wei Lu, Reasoning with latent structure refinement for document-level relation extraction, 2020, arXiv:2005.06312.

Dat Quoc Nguyen, and Karin Verspoor, Convolutional neural networks for chemical-disease relation extraction are improved with character-based word embeddings, 2018, arXiv:1805.10586.

Nanyun Peng, Hoifung Poon, Chris Quirk, Kristina Toutanova, and Wen-tau Yih, Cross-sentence N-ary relation extraction with graph LSTMs, 2017, arXiv:1708:03743.

Chris Quirk, and Hoifung Poon, Distant supervision for relation extraction beyond the sentence boundary, 2017, arXiv:1609.04873.

Sashank J. Reddi, Satyen Kale, Felix Yu, Dan Holtmann-Rice, Jiecao Chen, and Sanjiv Kumar, Stochastic negative mining for learning with large output spaces, 2019, arXiv:1810.07076.

Mike Schuster, and Kuldip K. Paliwal, Bidirectional recurrent neural networks, IEEE Transactions on Signal Processing, 1997, 45(11): 2673-2681.

Peng Shi, and Jimmy Lin, Simple BERT models for relation extraction and semantic role labeling, 2019, arXiv:1904.05255.

Livio Baldini Soares, Nicholas FitzGerald, Jeffrey Ling, and Tom Kwiatkowski, Matching the blanks: distributional similarity for relation learning, 2019, arXiv:1906.03158.

Linfeng Song, Yue Zhang, Zhiguo Wang, and Daniel Gildea, N-ary relation extraction using graph state LSTM, EMNLP, 2018, 2226-2235.

Hengzhu Tang, Yanan Cao, Zhenyu Zhang, Jiangxia Cao, Fang Fang, Shi Wang, and Pengfei Yin, HIN: hierarchical inference network for document-level relation extraction, Advances in Knowledge Discovery and Data Mining, 2020, 12084: 197-209.

Yun Tang, Jing Huang, Guangtao Wang, Xiaodong He, Bowen Zhou, Orthogonal relation transforms with graph context modeling for knowledge graph embedding, ACL, 2020, 2713-2722.

Ian Tenney, Dipanjan Das, and Ellie Pavlick, BERT rediscovers the classical NLP pipeline, ACL, 2019, 4593-4601.

Ashish Vaswani, Noam Shazeer, Niki Parmar, Jakob Uszkoreit, Llion Jones, Aidan N. Gomez, Lukasz Kaiser, and Illia Polosukhin, Attention is all you need, 2017, arXiv:1706.03762.

(56) References Cited

OTHER PUBLICATIONS

Patrick Verga, Emma Strubell, and Andrew McCallum, Simultaneously self-attending to all mentions for full-abstract biological relation extraction, NAACL-HLT, 2018, 872-884.

Jesse Vig, and Yonatan Belinkov, Analyzing the structure of attention in a transformer language model, 2019, arXiv:1906.04284.

Hong Wang, Christfried Focke, Rob Sylvester, Nilesh Mishra, and William Wang, Fine-tune BERT for DocRED with two-step process, 2019, arXiv:1909.11898.

Haoyu Wang, Ming Tan, Mo Yu, Shiyu Chang, Dakuo Wang, Kun Xu, Xiaoxiao Guo, and Saloni Potdar, Extracting multiple-relations in one-pass with pre-trained transformers, 2019, arXiv:1902.01030.

Linlin Wang, Zhu Cao, Gerard de Melo, and Zhiyuan Liu, Relation classification via multi-Level attention CNNs, ACL, 2016, 1298-1307.

Felix Wu, Tianyi Zhang, Amauri Holanda de Souza Jr, Christopher Fifty, Tao Yu, Kilian Q Weinberger, Simplifying graph convolutional networks, 2019, arXiv:1902.07153.

Ye Wu, Ruibang Luo, Henry C.M. Leung, Hing-Fung Ting, and Tak-Wah Lam, RENET: a deep learning approach for extracting gene-disease associations from literature, RECOMB, 2019, 272-284.

Yuan Yao, Deming Ye, Peng Li, Xu Han, Yankai Lin, Zhenghao Liu, Zhiyuan Liu, Lixin Huang, Jie Zhou, and Maosong Sun, DocRED: a large-scale document-level relation extraction dataset, ACL, 2019, 764-777.

Deming Ye, Yankai Lin, Jiaju Du, Zhenghao Liu, Peng Li, Maosong Sun, Zhiyuan Liu, Coreferential reasoning learning for language representation, 2020, arXiv:2004.06870.

Daojian Zeng, Kang Liu, Siwei Lai, Guangyou Zhou, and Jun Zhao, Relation classification via convolutional deep neural network, Coling, 2014, 2335-2344.

Yuhao Zhang, Peng Qi, and Christopher D. Manning, Graph convolution over pruned dependency trees improves relation extraction, EMNLP, 2018, 2205-2215.

\* cited by examiner

[John Stanistreet] was an Australian politician. He was born in [Bendigo] to legal manager John Jepson Stanistreet and Maud McIlroy. (...4 sentences...) In 1955 [John Stanistreet] was elected to the Victorian Legislative Assembly as the Liberal and Country Party member for [Bendigo.] [Stanistreet] died in [Bendigo] in 1971.

Subject: John Stanistreet    Object: Bendigo

Relation: place of birth; place of death

FIG. 2

Table 1

| Statistics / Dataset | DocRED | CDR | GDA |
|---|---|---|---|
| # Train | 3053 | 500 | 23353 |
| # Dev | 1000 | 500 | 5839 |
| # Test | 1000 | 500 | 1000 |
| # Relations | 97 | 2 | 2 |
| Avg.# entities per Doc. | 19.5 | 7.6 | 5.4 |

FIG. 7

Table 2

| Hyperparam / Dataset | DocRED | CDR | GDA |
|---|---|---|---|
| Batch size | 4 | 4 | 16 |
| # Epoch | 30 | 30 | 10 |
| Learning rate for encoder | 5e-5 | 54-5 | 54-5 |
| Learning rate for classifier | 1e-4 | 1e-4 | 1e-4 |
| Group size | 64 | 64 | 64 |
| Dropout | 0.1 | 0.1 | 0.1 |
| Gradient clipping | 1.0 | 1.0 | 1.0 |

FIG. 8

Table 3

| Model | Dev | | Test | |
|---|---|---|---|---|
| | Ign F1 | F1 | Ign F1 | F1 |
| *Sequence-based Models* | | | | |
| CNN (Yao et al. 2019) | 41.58 | 43.45 | 40.33 | 42.26 |
| BiLSTM (Yao et al. 2019) | 48.87 | 50.94 | 48.78 | 51.06 |
| *Graph-based Models* | | | | |
| BiLSTM-AGGCN (Guo, Zhang, and Lu 2019) | 46.29 | 52.47 | 48.89 | 51.45 |
| BiLSTM-LSR (Nan et al. 2020) | 48.82 | 55.17 | 52.15 | 54.18 |
| BERT-LSR$_{BASE}$ (Nan et al. 2020) | 52.43 | 59.00 | 56.97 | 59.05 |
| *Transformer-based Models* | | | | |
| BERT$_{BASE}$ (Wang et al. 2019a) | - | 54.16 | - | 53.20 |
| BERT-TS$_{BASE}$ (Wang et al. 2019a) | - | 54.42 | - | 53.92 |
| HIN-BERT$_{BASE}$ (Tang et al. 2020a) | 54.29 | 56.31 | 53.70 | 55.60 |
| CorefBERT$_{BASE}$ (Ye et al. 2020) | 55.32 | 57.51 | 54.54 | 56.96 |
| CorefRoBERTa$_{LARGE}$ (Ye et al. 2020) | 57.84 | 59.93 | 57.68 | 59.91 |
| *Our Methods* | | | | |
| BERT$_{BASE}$ (our implementation) | 54.27±0.28 | 56.39±0.18 | | |
| BERT-E$_{BASE}$ | 56.51±0.16 | 58.52±0.19 | | |
| BERT-ATLOP$_{BASE}$ | 59.22±0.15 | 61.09±0.16 | 59.31 | 61.30 |
| RoBERTa-ATLOP$_{LARGE}$ | 61.32±0.14 | 63.18±0.19 | 61.39 | 63.40 |

FIG. 9

Table 4

| Model | CDR | GDA |
|---|---|---|
| BRAN (Verga, Strubell, and McCallum 2018) | 62.1 | - |
| CNN (Nguyen and Verspoor 2018) | 62.3 | - |
| EoG (Christopoulou, Miwa, and Ananiadou 2019) | 63.6 | 81.5 |
| LSR (Nan et al. 2020) | 64.8 | 82.2 |
| SciBERTBASE (our implementation) | 65.1±0.6 | 82.5±0.3 |
| SciBERT-EBASE | 65.9±0.5 | 83.3±0.3 |
| SciBERT-ATLOPBASE | 69.4±1.1 | 83.9±0.2 |

FIG. 10

Table 5

| Model | Ign F1 | F1 |
|---|---|---|
| BERT-ATLOP$_{BASE}$ | 59.22 | 61.09 |
| —Adaptive Thresholding | 58.32 | 60.20 |
| —Localized Context Pooling | 58.19 | 60.12 |
| —Adaptive-Thresholding Loss | 39.52 | 41.74 |
| BERT-E$_{BASE}$ | 56.51 | 58.52 |
| —Entity Marker | 56.22 | 58.28 |
| —Group Bilinear | 55.51 | 57.54 |
| —Logsumexp Pooling | 55.35 | 57.40 |

FIG. 11

Table 6

| Strategy | Dev F1 Test | F1 |
|---|---|---|
| Global Thresholding | 60.14 | 60.62 |
| Per-class Thresholding | 61.73 | 60.35 |
| Adaptive Thresholding | 61.27 | 61.30 |

FIG. 12

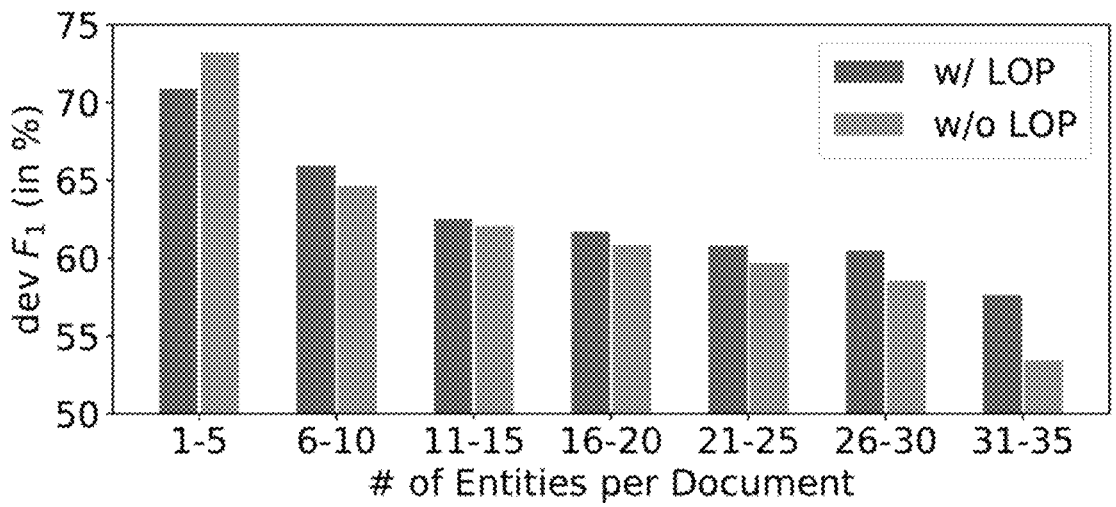

FIG. 13

*John Stanistreet was an Australian politician. He was born in Bendigo to legal manager John Jepson Stanistreet and Maud McIlroy. (... 4 sentences ...) In 1955 John Stanistreet was elected to the Victorian Legislative Assembly as the Liberal and Country Party member for Bendigo, but he was defeated in 1958. Stanistreet died in Bendigo in 1971.*

Subject: John Stanistreet  Object: Bendigo

Relation: place of birth; place of death

FIG. 14

SYSTEM AND METHOD FOR RELATION EXTRACTION WITH ADAPTIVE THRESHOLDING AND LOCALIZED CONTEXT POOLING

CROSS-REFERENCES

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entirety and to the same extent as if each reference were individually incorporated by reference.

FIELD OF THE DISCLOSURE

The present disclosure relates generally to relation extraction, and more specifically related to relation extraction using adaptive thresholding and localized context pooling.

BACKGROUND OF THE DISCLOSURE

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Relation extraction (RE), which extracts relations between pairs of entities in plain text, is an important task in Natural Language Processing (NLP). Relations can be extracted from sentences or documents. Comparing to sentence-level RE, document-level RE poses new challenges, because one document commonly contains multiple entity pairs, and one entity pair may occur multiple times in the document associated with multiple possible relations or multiple labels.

To tackle the multi-entity problem, most current approaches construct a document graph with dependency structures, heuristics, or structured attention, and then perform inference with graph neural models. The constructed graphs bridge entities that spread far apart in the document and thus alleviate the deficiency of RNN-based encoders in capturing long-distance information. However, as transformer-based models can implicitly model long-distance dependencies, it is unclear whether graph structures still help on top of pretrained language models such as BERT. There have also been approaches to directly apply pre-trained language models without introducing graph structures. They simply average the embedding of entity tokens to obtain the entity embeddings and feed them into the classifier to get relation labels. However, each entity has the same representation in different entity pairs, which can bring noise from irrelevant context.

Therefore, an unaddressed need exists in the art to address the multi-entity, multi label problem in document-level relation extraction.

SUMMARY OF THE DISCLOSURE

In certain aspects, the present disclosure provides two novel techniques, adaptive thresholding and localized context pooling, to solve the multi-label and multi-entity problems. The adaptive thresholding replaces the global threshold for multi-label classification in the prior work by a learnable entities-dependent threshold. The localized context pooling directly transfers attention from pre-trained language models to locate relevant context that is useful to decide the relation.

Specifically, the present disclosure provides the localized context pooling technique instead of introducing graph structures. The localized context pooling solves the problem of using the same entity embedding for all entity pairs. It enhances the entity embedding with additional context that is relevant to the current entity pair. Instead of training a new context attention layer from scratch, the disclosure directly transfers the attention heads from pre-trained language models to get entity-level attention. Then, for two entities in a pair, the disclosure merges their attentions by multiplication to find the context that is important to both of them.

For the multi-label problem, existing approaches reduce it to a binary classification problem. After training, a global threshold is applied to the class probabilities to get relation labels. This method involves heuristic threshold tuning and introduces decision errors when the tuned threshold from development data may not be optimal for all instances. In comparison, the present disclosure, provides the adaptive thresholding technique, which replaces the global threshold with a learnable threshold class. The threshold class is learned with an adaptive-threshold loss, which is a rank-based loss that pushes the logits of positive classes above the threshold and pulls the logits of negative classes below in model training. At the test time, the disclosure returns classes that have higher logits than the threshold class as the predicted labels or return NA if such class does not exist. This technique eliminates the need for threshold tuning, and also makes the threshold adjustable to different entity pairs, which leads to much better results.

By combining the adaptive thresholding and the localized context pooling, the present disclosure provides a simple yet novel and effective relation extraction model, named ATLOP (Adaptive Thresholding and Localized cOntext Pooling), to fully utilize the power of pre-trained language models. This model tackles the multi-label and multi-entity problems in document-level RE. Experiments on three document-level relation extraction datasets, DocRED, CDR, and GDA, demonstrate that the ATLOP model significantly outperforms the state-of-the-art methods. DocRED is a large-scale document-level relation extraction dataset constructed from Wikipedia and Wikidata, CDR is a dataset for chemical-disease relations, and GDA is a dataset for gene-disease associations.

In certain aspects, the present disclosure relates to a system. In certain embodiments, the system includes a computing device, and the computing device has a processer and a storage device storing computer executable code. The computer executable code, when executed at the processor, is configured to:

provide a document;

embed a plurality of entities in the document into a plurality of embedding vectors; and predict one of a plurality of relations between a first entity in the document and a second entity in the document based on a first embedding vector and a second embedding vector, the first embedding vector of the plurality of embedding vectors representing the first entity, and the second embedding vector of the plurality of embedding vectors representing the second entity, where the computer executable code is configured to embed and predict using a language model stored in the computing device, each of the plurality of relations has an adaptive threshold, and the one of the plurality of relations is determined to exist when a logit of the relation is greater than a logit function of corresponding one of the adaptive thresholds of the relations.

In certain embodiments, the computer executable code is configured to embed each of the plurality of entities by summarizing at least one hidden representation of at least one mention of the entity using LogSumExp (LSE).

In certain embodiments, the computer executable code is configured to predict one of a plurality of relations by calculating a local context pooling for a pair of entities selected from the plurality of entities using:

$$A^{(s,o)} = A_s^E \cdot A_o^E,$$

$$q^{(s,o)} = \sum_{i=1}^{H} A_i^{(s,o)},$$

$$a^{(s,o)} = q^{(s,o)}/1^T q^{(s,o)}, \text{ and}$$

$$c^{(s,o)} = H^T a^{(s,o)},$$

where the pair of entities has a subject entity and an object entity, $A_s^E$ is a token-level attention of the subject entity, $A_o^E$ is a token-level attention of the object entity, $A^{(s,o)}$ is a multiplication of $A_s^E$ and $A_o^E$, H in $\sum_{i=1}^{H} A_i^{(s,o)}$ is a number of attention heads, $A_i^{(s,o)}$ is an i-th multiplication of H multiplications, $a^{(s,o)}$ is normalization of $q^{(s,o)}$ to sum 1, H in $H^T a^{(s,o)}$ is the last layer embedding of pre-trained language models, and $c^{(s,o)}$ is the local context pooling for the pair of entities.

In certain embodiments, hidden states of the subject entity and the object entity are determined by:

$$z_s^{(s,o)} = \tanh(W_s h_{e_s} + W_{C1} c^{(s,o)}), \text{ and}$$

$$z_o^{(s,o)} = \tanh(W_o h_{e_o} + W_{C2} c^{(s,o)}),$$

where $h_{e_s}$ is the embedding of the subject entity, $z_s^{(s,o)}$ is hidden state of the subject entity, $h_{e_o}$ is the embedding of the object entity, $z_o^{(s,o)}$ is hidden state of the object entity, and $W_s$, $W_o$, $W_{C1}$, and $W_{C2}$ are model parameters.

In certain embodiments, the computer executable code is configured to predict relation between the subject entity and the object entity using:

$$logit_r = \sum_{i=1}^{k} z_s^{iT} W_r^i z_o^i + b_r,$$

where $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, and $W_r^i$ and $b_r$ are model parameters. When the $logit_r$ is greater than a logit function of a learnable threshold TH of the relation r, the subject entity $e_s$ and the object entity $e_o$ have the relation r. In certain embodiments, wherein the dimensions of the $z_s^{(s,o)}$ and the dimensions of the $z_o^{(s,o)}$ are 768, and k is 12.

In certain embodiments, the language model includes at least one of a bidirectional encoder representations from transformer (BERT), a robustly optimized BERT approach (roBERTa), SciBERT, a generative pre-training model (GPT), a GPT-2, and a reparameterized transformer-XL network (XLnet).

In certain embodiments, the language model has a BERT based architecture, and loss function for training the language model is determined by:

$$logit_r = \sum_{i=1}^{k} z_s^{iT} W_r^i z_o^i + b_r,$$

$$L_1 = -\sum_{r \in P_T} \log\left(\frac{\exp(logit_r)}{\sum_{r' \in P_T \cup \{TH\}} \exp(logit_{r'})}\right),$$

$$L_2 = -\log\left(\frac{\exp(logit_{TH})}{\sum_{r' \in N_T \cup \{TH\}} \exp(logit_{r'})}\right), \text{ and}$$

$$L = L_1 + L_2,$$

where $logit_r$ is the logit function of the subject entity $e_s$ and the object entity $e_o$, r represents a relation, k is a positive integer, dimensions of the $z_s^{(s,o)}$ are divided by k to form a plurality of $z_s^i$, dimension of the $z_o^{(s,o)}$ are divided by k to form a plurality of $z_o^i$, $W_r^i$ and $b_r$ are model parameters, TH is a learnable threshold of the relation, $P_T$ represents positive classes of relations, NT represents negative classes of relations. In certain embodiments, wherein the dimensions of the $z_s^{(s,o)}$ and the dimensions of the $z_o^{(s,o)}$ are 768, and k is 12.

In certain embodiments, the computer executable code is further configured to: use the first entity, the second entity, and the predicted one of the plurality of relations between the first entity and the second entity to construct a knowledge graph. The knowledge graph may be, for example, a general knowledge graph containing human knowledge, a fashion graph containing features of fashion products, a gene-disease graph containing relationships between human genes and human diseases related to the genes, or a chemical-disease graph containing relations between chemicals and diseases.

In certain embodiments, the computer executable code is further configured to, when a question includes the first entity and the second entity, and the document is predetermined to contains an answer to the question: use the predicted one of the plurality of relations to form the answer.

In certain aspects, the present disclosure relates to a method. In certain embodiments, the method includes:
providing, by a computing device, a document;
embedding, by a computing device, a plurality of entities in the document into a plurality of embedding vectors; and
predicting, by a computing device, one of a plurality of relations between a first entity in the document and a second entity in the document based on a first embedding vector and a second embedding vector, the first embedding vector of the plurality of embedding vectors representing the first entity, and the second embedding vector of the plurality of embedding vectors representing the second entity,
where the steps of embedding and predicting are performed by a language model stored in the computing device, each of the plurality of relations has an adaptive threshold, and the one of the plurality of relations is determined to exist when a logit of the relation is greater than a logit function of corresponding one of the adaptive thresholds of the relations.

In certain embodiments, the steps of embedding of each of the plurality of entities is performed by summarizing at least one hidden representation of at least one mention of the entity using LogSumExp (LSE).

In certain embodiments, the step of predicting includes calculating a local context pooling for a pair of entities selected from the plurality of entities using:

$$A^{(s,o)} = A_s^E \cdot A_o^E,$$

$$q^{(s,o)} = \sum_{i=1}^{H} A_i^{(s,o)},$$

$$a^{(s,o)} = q^{(s,o)} / 1^T q^{(s,o)}, \text{ and}$$

$$c^{(s,o)} = H^T a^{(s,o)},$$

where the pair of entities comprises a subject entity and an object entity, $A_s^E$ is a token-level attention heads of the subject entity, $A_o^E$ is a token-level attention heads of the object entity, $A^{(s,o)}$ is a multiplication of $A_s^E$ and $A_o^E$, H in $\Sigma_{i=1}^{H} A_i^{(s,o)}$ is a number of attention heads, $A_i^{(s,o)}$ is an i-th multiplication of H multiplications, $a^{(s,o)}$ is normalization of $q^{(s,o)}$ to sum 1, H in $H^T a^{(s,o)}$ is the last layer embedding of pre-trained language models, and $c^{(s,o)}$ is the local context pooling for the pair of entities.

In certain embodiments, hidden states of the subject entity and the object entity are determined by:

$$z_s^{(s,o)} = \tanh(W_s h_{e_s} + W_{C1} c^{(s,o)}), \text{ and}$$

$$z_o^{(s,o)} = \tanh(W_o h_{e_o} + W_{C2} c^{(s,o)}),$$

where $h_{e_s}$ is the embedding of the subject entity, $z_s^{(s,o)}$ is hidden state of the subject entity, $h_{e_o}$ is the embedding of the object entity, $z_o^{(s,o)}$ is hidden state of the object entity, and $W_s$, $W_o$, $W_{C1}$, and $W_{C2}$ are model parameters.

In certain embodiments, the step of predicting relation between the subject entity and the object entity is performed using:

$$logit_r = \sum_{i=1}^{k} z_s^{iT} W_r^i z_o^i + b_r,$$

where $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, and $W_r^i$ and $b_r$ are model parameters. When the $logit_r$ is greater than the logit of a learnable threshold TH of the relation r, the subject entity $e_s$ and the object entity $e_o$ have the relation r.

In certain embodiments, the language model comprises a bidirectional encoder representations from transformer (BERT), SciBERT and the loss function for training the language model is determined by:

$$logit_r = \sum_{i=1}^{k} z_s^{iT} W_r^i z_o^i + b_r,$$

$$L_1 = -\sum_{r \in P_T} \log\left(\frac{\exp(logit_r)}{\sum_{r' \in P_T \cup \{TH\}} \exp(logit_{r'})}\right),$$

$$L_2 = -\log\left(\frac{\exp(logit_{TH})}{\sum_{r' \in N_T \cup \{TH\}} \exp(logit_{r'})}\right), \text{ and}$$

$$L = L_1 + L_2,$$

where $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, $W_r^i$ and $b_r$ are model parameters, TH is a learnable threshold of the relation, $P_T$ represents positive classes of relations, and NT represents negative classes of relations.

In certain embodiments, the method further includes: using the first entity, the second entity, and the predicted one of the plurality of relations between the first entity and the second entity to construct a knowledge graph In certain embodiments, the method further includes, when a question includes the first entity and the second entity, and the document is predetermined to comprise an answer to the question: using the predicted one of the plurality of relations to form the answer.

In certain aspects, the present disclosure relates to a non-transitory computer readable medium storing computer executable code. The computer executable code, when executed at a processor of a computing device, is configured to perform the method described above.

These and other aspects of the present disclosure will become apparent from following description of the preferred embodiment taken in conjunction with the following drawings and their captions, although variations and modifications therein may be affected without departing from the spirit and scope of the novel concepts of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

FIG. 2 schematically depicts an example from DocRED dataset.

FIG. 7, Table 1 shows statistics of the datasets in experiments, where Ent., Ment., and Doc. Are abbreviations of entity, mentions, and document, respectively.

FIG. 8, Table 2 shows hyper parameters of the ATLOP application according to certain embodiments of the present disclosure.

FIG. 9, Table 3 shows results on the development and test set of DocRED. The table reports mean and standard deviation of $F_1$ on the development set by conducting five runs of training using different random seeds. The table reports the official test score of the best checkpoint on the development set.

FIG. 10, Table 4 shows test $F_1$ score (in %) on CDR and GDA dataset. The table reports mean and standard deviation of $F_1$ on the test set by conducting five runs of training using different random seeds.

FIG. 11, Table 5 shows ablation study of ATLOP on DocRED. We turn off different component of the model one at a time. We report the average dev $F_1$ score by conducting five runs of training using different seeds.

FIG. 12, Table 6 shows result of different thresholding strategies on DocRED. Our adaptive thresholding consistently outperforms other strategies on the test set.

FIG. 13 shows Dev F1 score of documents with different number of entities on DocRED. Our localized context pooling achieves better result when the number of entities is larger than five. The improvement becomes more significant when the number of entities increases.

FIG. 14 shows context weights of the example in FIG. 2 using localized context poling according to certain embodiments of the present disclosure.

DETAILED DESCRIPTION

Figure 1:
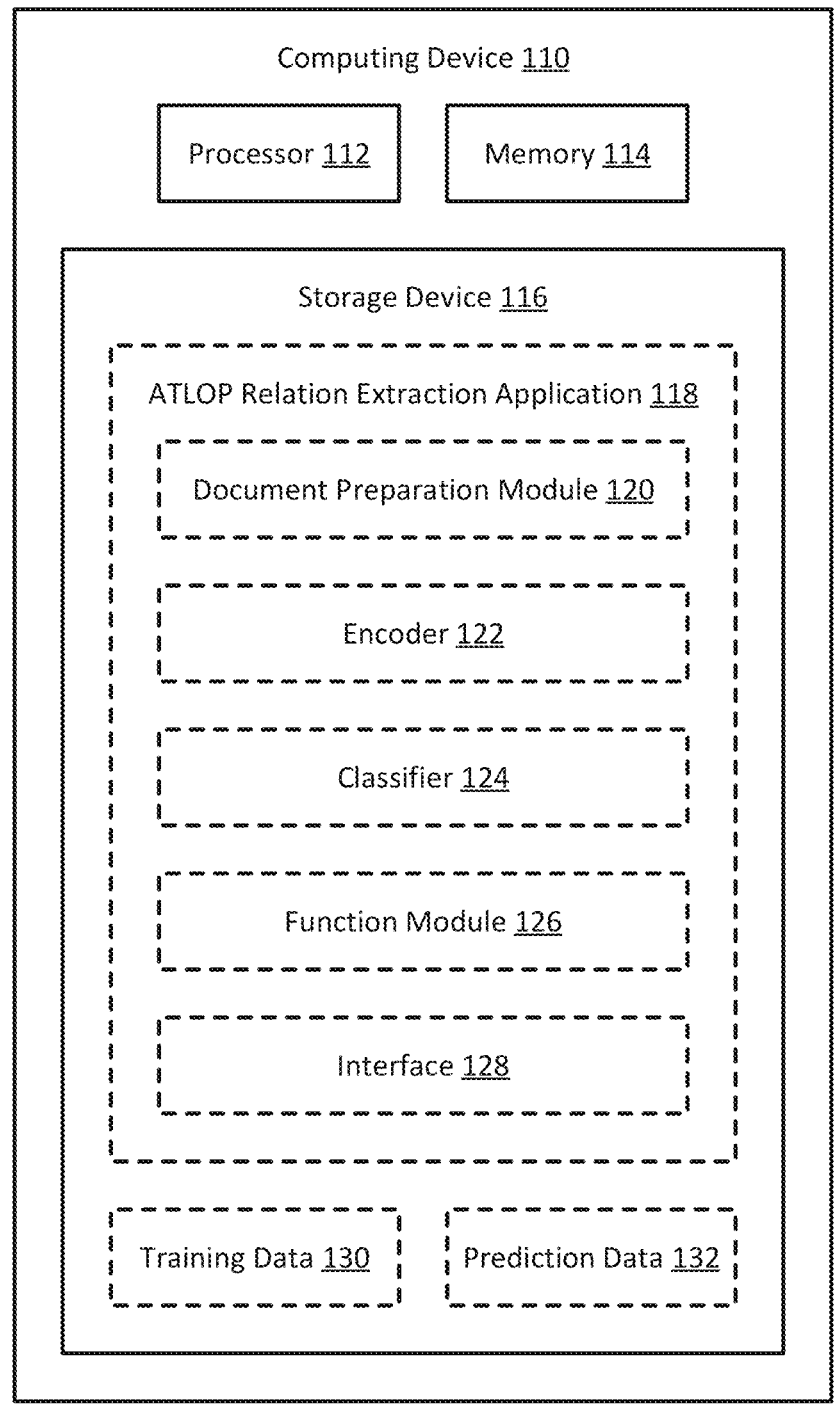
FIG. 1 schematically depicts an adaptive thresholding and localized context pooling (ATLOP) system according to certain embodiments of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that same thing can be said in more than one way. Consequently, alternative language and synonyms may be used for any one or more of the terms discussed herein, nor is any special significance to be placed upon whether or not a term is elaborated or discussed herein. The use of examples anywhere in this specification including examples of any terms discussed herein is illustrative only, and in no way limits the scope and meaning of the disclosure or of any exemplified term. Likewise, the disclosure is not limited to various embodiments given in this specification.

As used herein, the term "module" may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term "code", as used herein, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The term "interface", as used herein, generally refers to a communication tool or means at a point of interaction between components for performing data communication between the components. Generally, an interface may be applicable at the level of both hardware and software, and may be uni-directional or bi-directional interface. Examples of physical hardware interface may include electrical connectors, buses, ports, cables, terminals, and other I/O devices or components. The components in communication with the interface may be, for example, multiple components or peripheral devices of a computer system.

The present disclosure relates to computer systems. As depicted in the drawings, computer components may include physical hardware components, which are shown as solid line blocks, and virtual software components, which are shown as dashed line blocks. One of ordinary skill in the art would appreciate that, unless otherwise indicated, these computer components may be implemented in, but not limited to, the forms of software, firmware or hardware components, or a combination thereof.

The apparatuses, systems and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure will now be described more fully hereinafter with reference to the accompanying drawings, in which embodiments of the present disclosure are shown. This disclosure may, however, be embodied in many different forms and should not be construed as limited to the embodiments set forth herein; rather, these embodiments are provided so that this disclosure will be thorough and complete, and will fully convey the scope of the present disclosure to those skilled in the art.

FIG. 1 schematically depicts an Adaptive Thresholding and Localized cOntext pooling (ATLOP) system according to certain embodiments of the present disclosure. As shown in FIG. 1, the system 100 includes a computing device 110. In certain embodiments, the computing device 110 may be a server computer, a cluster, a cloud computer, a general-purpose computer, a headless computer, or a specialized computer, which provides relation prediction and evidence prediction. The computing device 110 may include, without being limited to, a processor 112, a memory 114, and a storage device 116. In certain embodiments, the computing device 110 may include other hardware components and software components (not shown) to perform its corresponding tasks. Examples of these hardware and software components may include, but not limited to, other required memory, interfaces, buses, Input/Output (I/O) modules or devices, network interfaces, and peripheral devices.

The processor 112 may be a central processing unit (CPU) which is configured to control operation of the computing device 110. The processor 112 can execute an operating system (OS) or other applications of the computing device 110. In certain embodiments, the computing device 110 may have more than one CPU as the processor, such as two CPUs, four CPUs, eight CPUs, or any suitable number of CPUs.

The memory 114 can be a volatile memory, such as the random-access memory (RAM), for storing the data and information during the operation of the computing device 210. In certain embodiments, the memory 114 may be a volatile memory array. In certain embodiments, the computing device 110 may run on more than one memory 114.

The storage device 116 is a non-volatile data storage media for storing the OS (not shown) and other applications of the computing device 110. Examples of the storage device 116 may include non-volatile memory such as flash memory, memory cards, USB drives, hard drives, floppy disks, optical drives, solid-state drive, or any other types of data storage devices. In certain embodiments, the computing device 110 may have multiple storage devices 116, which may be identical storage devices or different types of storage devices, and the applications of the computing device 110 may be stored in one or more of the storage devices 116 of the computing device 110.

In this embodiments, the processor 112, the memory 114, and the storage device 116 are component of the computing device 110, such as a server computing device. In other embodiments, the computing device 110 may be a distributed computing device and the processor 112, the memory 114, and the storage device 116 are shared resources from multiple computing devices in a pre-defined area.

The storage device 116 includes, among other things, an ATLOP relation extraction application 118, training data 130 and prediction data 132. The ATLOP relation extraction application 118 is configured to train its model structure using the training data 130 and make predictions from the prediction data 132. The training data 130 and the prediction data 132 are optional for the computing device 110, as long as the training and prediction data stored in other devices is accessible to the ATLOP relation extraction application 118.

As shown in FIG. 1, the ATLOP relation extraction application 118 includes a document preparation module 120, an encoder 122, a classifier 124, a function module 126, and an interface 128. In certain embodiments, the ATLOP relation extraction application 118 may include other applications or modules necessary for the operation of the ATLOP relation extraction application 118. It should be noted that the modules 120-128 are each implemented by computer executable codes or instructions, or data table or databases, or a combination of hardware and software, which collectively forms one application. In certain embodiments, each of the modules may further include sub-modules. Alternatively, some of the modules may be combined as one stack. In other embodiments, certain modules may be implemented as a circuit instead of executable code. In certain embodiments, the modules can also be collectively named a model, which can be trained using training data, and after well trained, can be used to make a prediction.

The document preparation module 120 is configured to prepare training samples or query samples, and send the prepared training samples or query samples to the encoder 122. Given a training sample or query sample such as a document d, and a set of entities $\{e_i\}_{i=1}^n$, the document preparation module 120 is configured to define a set of relations R and a relation {NA}. The relation {NA} means no relation. For the training sample, the document preparation module 120 is further configured to provide ground truth labels of the relations corresponding to the entities. In certain embodiments, when the training sample or query samples are in a format consistent with the requirements of the encoder 122 and the classifier 124, the document preparation module 120 may simply input the samples to the encoder 122 and the classifier 124. In certain embodiments, when the training sample or query samples are in a format slightly different from the requirements of the encoder 122 and the classifier 124, the document preparation module 120 may revise the format such that the revised format is consistent with the requirements of the encoder 122 and the classifier 124.

Given the document d, the set of entities $\{e_i\}_{i=1}^n$, the predefined set of relations R, and the relation {NA}, the task of document-level relation extraction is to predict a subset of relations from $R \cup \{NA\}$ between the entity pairs $(e_s, e_o)_{s,o=1 \ldots n; s \neq o}$, where R is the pre-defined set of relations of interest, $e_s$ and $e_o$ are identified as subject and object entities, respectively, n is a total number of predefined entities, and n is a positive integer. The entity $e_i$ may occur multiple times in the document d by entity mentions $$\{m_j^i\}_{j=1}^{N_{e_i}},$$

where N is a positive integer indicating the number of mentions of the entity $e_i$ in the document d, and $m_j^i$ is the j-th mention of the entity $e_i$ in the document d. A relation exists between entities $(e_s, e_o)$ if it is expressed by any pair of their mentions. The entity pairs that do not express any relation are labeled NA. At the training time, the model needs to predict the labels of all entity pairs $(e_s, e_o)_{s,o=1 \ldots n; s \neq o}$ in the document d and compare the prediction with the ground true label. At the test time or query time, the model needs to predict the labels of all entity pairs $(e_s, e_o)_{s,o=1 \ldots n; s \neq o}$ in the document d.

FIG. 2 schematically depicts an example from DocRED dataset. As shown in FIG. 2, the subject entity is "John Stanistreet," the object entity is "Bendigo," the relations are "place of birth" and "place of death." The "place of birth" relation is expressed in the first two sentences, and the "place of death" relation is expressed in the last sentence. The other entities in the document are also highlighted, but are irrelevant to the entity tuple of "John Stanistreet-Bendigo."

Referring back to FIG. 1, the encoder 122 and the classifier 124 are based on a language model, such as BERT, and are improvement of the language model. The encoder 122 is configured to, upon receiving the prepared document sample from the document preparation module 120, encode the document to entity embeddings in the form of vectors, and send the entity embeddings to the classifier 124. For a given document d, firstly, the encoder 122 is configured to recognize the entities via named-entity recognition (NER) such as spaCy, Stanza, Unified Medical Language Systems (UMLS) or Gene Ontology (GO), and marks the entities for example by their spans. Kindly note that for training data, the entities and relation labels are provided and there is no need to perform NER; and during inference, the possible entities and possible relations may also be provided, and the NER may not be necessary. Each entity may have multiple mentions in the document. Then the encoder 122 is configured to mark the position of the entity mentions by inserting a special symbol "*" at the start and the end of each mentions. After marking the mentions, the encoder 122 is configured to convert the documents containing the "*" marks into tokens, where each "*" is a token. Therefore, the document d is now represented by tokes, i.e. $d=\{x_t\}_{t=1}^{l}$, where l is a positive integer indicating the total number of tokens, and $x_t$ is the t-th of the l tokens. The documents represented by the tokens are fed into a pre-trained language model, such as BERT, to obtain the contextual embedding:

$$[h_1, h_2, \ldots, h_t, \ldots, h_l] = \text{BERT}([x_1, x_2, \ldots, x_t, \ldots, x_l]) \qquad (1)$$

Here $h_t$ is a hidden vector or embedding of the token $x_t$.

After the embedding of the tokens, the encoder 122 is further configured to take the embedding of the start "*" in front of an entity mention as the embedding of that entity mention. In certain embodiments, the disclose may also use the end the end "*" after the entity as the mention. For the entity $e_i$ with mentions $$\{m_j^i\}_{j=1}^{N_{e_i}},$$

the encoder 12 is then configured to apply log sum exp pooling, a smooth version of max pooling, to get the entity embedding $h_{e_i}$, $$h_{e_i} = \log \sum_{j=1}^{N_{e_i}} \exp(h_{m_j}) \qquad (2)$$

Here $m_j^i$ is the j-th mention of the entity $e_i$ in the document d, $N_{e_i}$ is a positive integer indicating the total number of entity mentions of the entity $e_i$, and $h_{m_j}$ is the embedding of the j-th entity mention of the entity $e_i$ in the document d. The pooling accumulates signals from mentions in the documents, and the pooling shows better performance compared to mean pooling.

The classifier 124 is configured to, upon receiving the entity embedding, predict relations between any two of the entities, and send the relations to the function module 126. Given the embeddings $(h_{e_s}, h_{e_o})$ of an entity pair $e_s$, $e_o$ computed by equation (2), the classifier 124 is configured to map the entities to hidden states z with a linear layer followed by non-linear activation, then calculate the probability of relation r by bilinear function and sigmoid activation. This process is formulated as:

$$z_s = \tanh(W_s h_{e_s}) \qquad (3)$$

$$z_o = \tanh(W_o h_{e_o}) \qquad (4)$$

$$P(r|e_s, e_o) = \sigma(z_s^T W_r z_o + b_r)$$

Here $W_s \in \mathbb{R}^{d \times d}$, $W_o \in \mathbb{R}^{d \times d}$, $W_r \in \mathbb{R}^{d \times d}$, $b_r \in \mathbb{R}$ are model parameters, and d is dimensions of the embedding vectors. $z_s$ is the hidden state of the subject entity, $z_o$ is the hidden state of the object entity, tanh is the hyperbolic tangent function, $W_s$ is the weight for the subject entity embedding $h_{e_s}$, $W_o$ is the weight for the object entity embedding $h_{e_o}$, $W_r$ is the weight for the relation r, and $b_r$ is a learnable constant for the relation r.

The representation of one entity is the same among different entity pairs. To reduce the number of parameters in the bilinear classifier, the classifier 124 is configured to use the group bilinear, which splits the embedding dimensions into k equal-sized groups and applies bilinear within the groups:

$$[z_s^1; \ldots; z_s^i; \ldots; z_s^k] = z_s, \qquad (5)$$
$$[z_o^1; \ldots; z_o^i; \ldots; z_o^k] = z_o,$$
$$P(r|e_s, e_o) = \sigma\left(\sum_{i=1}^{k} z_s^{iT} W_r^i z_o^i + b_r\right)$$

Here $W_r^i \in \mathbb{R}^{d/k \times d/k}$ for $i=1 \ldots k$ are model parameters. $P(r|e_s, e_o)$ is the probability that relation r is associated with the entity pair $(e_s, e_o)$. In certain embodiments, k=12 and d=768, and thus each of the 12 $z_s^i$ contains 64 dimensions of the total of 768 dimensions of the $z_s$. In this way, the disclosure can reduce the number of parameters from $d^2$ to $d^2/k$. In certain embodiments, the number of vector dimensions and the k may have other values according to the situation.

In certain embodiments, instead of calculating the P ($r|e_s, e_o$), the classifier 124 calculates $$logit_r = \sum_{i=1}^{k} z_s^{iT} W_r^i z_o^i + b_r,$$

where $logit_r$ is a logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, and $W_r^i$ and $b_r$ are model parameters. When the $logit_r$ is greater than a learnable threshold TH of the relation r or is greater than the logit of the learnable threshold TH, the subject entity $e_s$ and the object entity $e_o$ have the relation r.

The classifier 124 may use the binary cross entropy loss for training. During inference, the classifier 124 may tune a global threshold θ that maximizes evaluation metrics ($F_1$ score for RE) on the development set and return r as an associated relation if $P(r|e_s, e_o) > θ$ or return NA if no relation exists. The application of the above described log sum exp pooling in the encoder 122 and the application of the group bilinear in the classifier 124 enhance the performance of the disclosure, which out performance that of a state-of-the-art language model, such as BERT.

In certain embodiments, the classifier 124 is further improved by replacing the global threshold θ in the model with an adaptive thresholding. The classifier 124 outputs the probability P ($r|e_s, e_o$) within the range [0, 1], which needs thresholding to be converted to relation labels. As the threshold neither has a closed-form solution nor is differentiable, a common practice for deciding threshold is enumerating several values in the range [0, 1] and picking the one that maximizes the evaluation metrics ($F_1$ score for RE). However, the model may have different confidence for different entity pairs or classes in which one global threshold does not suffice. The number of relations varies (multi-label problem) and the models may not be globally calibrated so that the same probability does not mean the same for all entity pairs. To solve the problem, the classifier 124 is configured to replace the global threshold with a learnable, adaptive one, which can reduce decision errors during inference.

For the convenience of explanation, the disclosure splits the labels of entity pair $T=(e_s, e_o)$ into two subsets: positive labels $P_T$ and negative labels $N_T$, which are defined as follows:

Positive labels $P_T \in R$ are the relations that exist between the entities in T. If T does not express any relation, $P_T$ is empty.

Negative labels $N_T \in R$ are the relations that do not exist between the entities. If T does not express any relation, $N_T=R$.

If an entity pair is classified correctly, the logit function (or the log-odds) of positive labels should be higher than the threshold while those of negative labels should be lower. The classifier 124 is configured to introduce a threshold class TH, which is automatically learned in the same way as other classes (see equation (5)). At the test time, the classifier 124 is configured to return classes with higher logits than the TH class as positive labels or return NA if such classes do not exist. This threshold class learns an entities-dependent threshold value. It is a substitute for the global threshold and thus eliminates the need for tuning threshold on the development set. In certain embodiments, as described above, the classifier 124 is configured to calculate the logit $logit_r$ instead of the probability, and the $logit_r$ is compared with the logit of the TH to determine if the relation r exist or not.

To learn the new model, the classifier 124 is configured to define a special loss function that considers the TH class. Specifically, the classifier is configured to design the adaptive thresholding loss based on the standard categorical cross entropy loss. The loss function is broken down to two parts as shown below:

$$L_1 = -\sum_{r \in P_T} \log\left(\frac{\exp(logit_r)}{\sum_{r' \in P_T \cup \{TH\}} \exp(logit_{r'})}\right),$$

$$L_2 = -\log\left(\frac{\exp(logit_{TH})}{\sum_{r' \in N_T \cup \{TH\}} \exp(logit_{r'})}\right),$$

$$L = L_1 + L_2.$$

The first part $L_1$ involves positive labels and the TH class. Since there may be multiple positive labels, the total loss is calculated as the sum of categorical cross entropy losses on all positive labels. $L_1$ pushes the logits of all positive labels to be higher than the TH class. It is not used if there is no positive label. The second part $L_2$ involves the negative classes and threshold class. It is a categorical cross entropy loss with TH class being the true label. It pulls the logits of negative labels to be lower than the TH class. Two parts are simply summed as the total loss.

Figure 3:
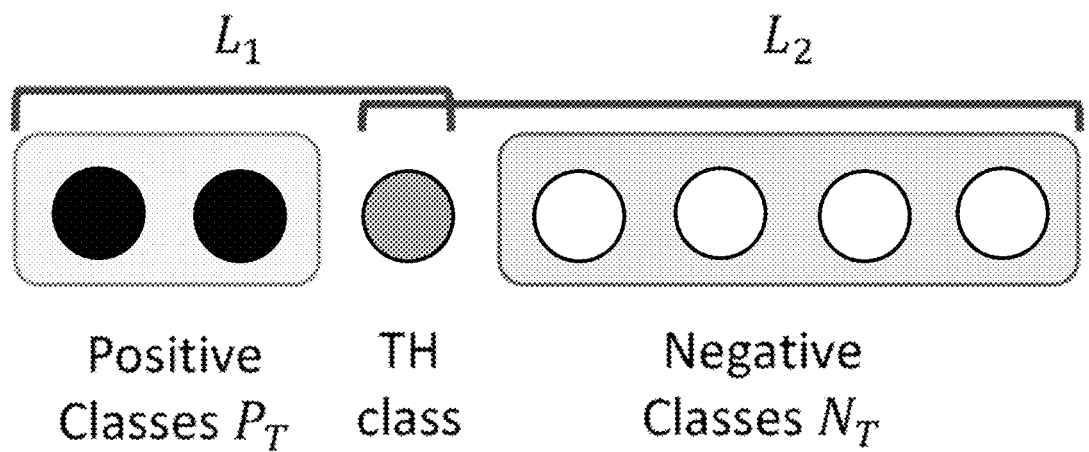
FIG. 3 schematically depicts the adaptive-thresholding loss according to certain embodiments of the present disclosure.

FIG. 3 schematically depicts the adaptive-thresholding loss according to certain embodiments of the present disclosure. As shown in FIG. 3, the L1 loss considers the positive classes $P_T$ and the TH class, and the L2 loss considers the TH class and the negative class $N_T$. Comparing with the global threshold, the classifier 124 achieves a large performance gain.

To accurately locating contexts that are closely related to the entity pair relation, the present disclosure further improves the pooling in the encoder 122, which consequently affect the hidden states in the classification by the classifier 124. Specifically, the log sum exp pooling shown in the equation (2) accumulates the embedding of all mentions for an entity across the whole document and generates one embedding for this entity. The entity embedding is then used in the classification of all entity pairs. However, since some context may express relations unrelated to the entity pair, it is better to have a localized representation that only attends to the relevant context in the document that is useful to decide to relation(s) for the entity pair.

Accordingly, the disclosure provides the localized context pooling, which enhances the embedding of an entity pair with an additional context embedding that is related to both entities. In certain embodiments, since the disclosure uses pre-trained transformer-based models as the encoder 122, which has already learned token-level dependencies by multi-head self-attention, the disclosure considers directly using their attention heads for localized context pooling. This method transfers the well-learned dependencies from the pre-trained language model without learning new attention layers from scratch.

Specifically, the disclosure uses the token-level attention heads A from the last transformer layer in the pre-trained language model, where attention $A_{ijk, 1 \leq i \leq H, 1 \leq j, k \leq 1}$ represents the importance of token k to token j in the i-th of a total of H attention head. For entity mention that spans from the j'-th token ("*" symbol), the disclosure takes $A_{j=j'}$ as the mention-level attention, then averages the attention over mentions of the same entity to obtain entity-level attentions $\{A_i^E\}_{i=1}^m$, where each attention $A_j^E \in \mathbb{R}^{H \times L}$ denotes the importance of context tokens to the i-th entity in H attention heads (H for example can be 12 in BERT). Then for entity pair $(e_s, e_o)$, the disclosure obtains the context tokens that are important to both entities by multiplying their entity-level attentions followed by normalization:

$$A^{(s,o)} = A_s^E \cdot A_o^E,$$

$$q^{(s,o)} = \sum_{i=1}^{H} A_i^{(s,o)},$$

$$a^{(s,o)} = q^{(s,o)} / 1^T q^{(s,o)},$$

which means the total of the vector dimensions in $q^{(s,o)}$ is normalized to be 1, that is, the summation of the dimensions of the $a^{(s,o)}$ vector is 1, $c^{(s,o)} = H^T a^{(s,o)}$, the number dimensions of $c^{(s,o)}$ for example, may be 768.

Here $c^{(s,o)}$ is the localized contextual embedding for $(e_s, e_o)$. The contextual embedding is fused into the pooled entity embedding to obtain entity representations that are different for different entity pairs, by modifying the original linear layer in the equations (3) and (4) as follows:

$$z_s^{(s,o)} = \tanh(W_s h_{e_s} + W_{C1} c^{(s,o)}) \quad (6)$$

$$z_o^{(s,o)} = \tanh(W_o h_{e_o} + W_{C2} c^{(s,o)}) \quad (7)$$

where $W_{C1}, W_{C1} \in \mathbb{R}^{d \times d}$ are model parameters.

Figure 4:
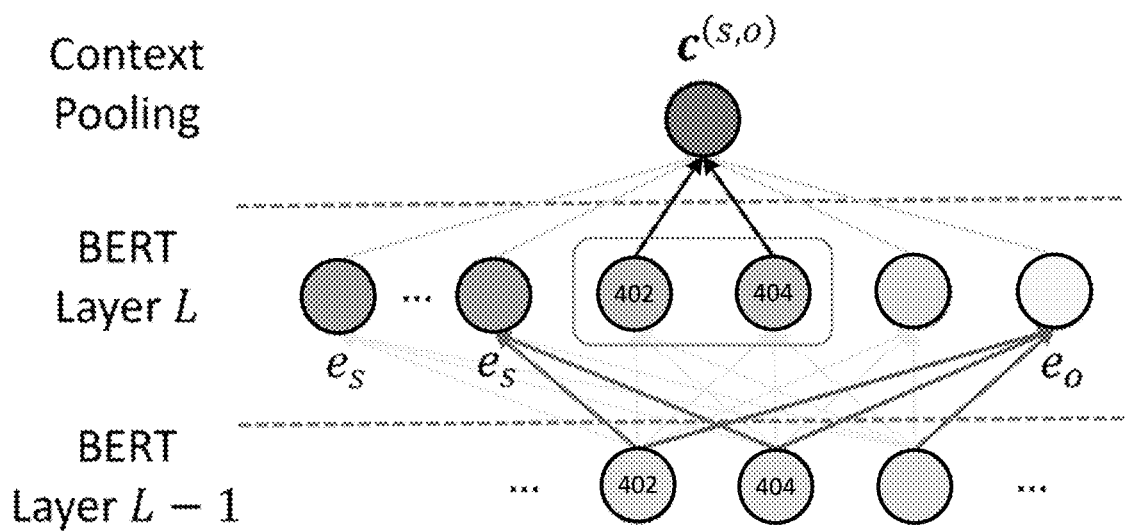
FIG. 4 schematically depicts localized context pooling according to certain embodiments of the present disclosure.

FIG. 4 schematically depicts the localized context pooling according to certain embodiments of the present disclosure. As shown in FIG. 4, the tokens at the same column are the same tokens at different layers, tokens are weighted averaged to form the localized context $c^{(s,o)}$ of the entity pair $(e_s, e_o)$. The weights of tokens are derived by multiplying the attention weights of the subject entity $e_s$ and the object entity $e_o$ from the last transformer layer so that only the tokens 402 and 404 that are important to both entities receive higher weights.

Kindly note i in different context of the present disclosure may have different meanings. For example, the i in $e_i$ is a positive integer and represents the i-th of the entities; the i in $z_s^i$ is a positive integer and represents the i-th of the k components of the hidden representation $z_s$; the i in $z_o^i$ is a positive integer and represents the i-th of the k components of the hidden representation $z_o$; the i in $A_{ijk, 1 \le i \le H, 1 \le j,k \le l}$ is a positive integer between 1 to H and represents the i-th of the H attentions; the i in $\{A_i^E\}_{i=1}^m$ is a positive integer between 1 to m and represents the attention of the i-th entity.

Referring back to FIG. 1, the function module 126 is configured to, when the document preparation module 120, the encoder 122, and the classifier 124 make the prediction of relations, use the predicted relations to perform a function. In certain embodiments, the function is to construct a knowledge graph, and the function module 126 is configured to incorporate the entity pairs and the predicted relations of the entity pairs into the knowledge graph. Each entity may be a node in the knowledge graph, and the relations may be the edges linking the corresponding entities. In certain embodiments, the function is information retrieval from a database, and the function module 126 is configured to use a training dataset for the database to train the encoder 122 and the classifier 124, infer relationships from the database after training, and provide the entity pairs and its relationships to a user. In certain embodiments, the function is a question and answer system, and the function module 126 is configured to extract entities from the question, infer entity relationships from an answer database or comment database, use the entities extracted from the question and the inferred relationship to form an answer to the question, and provide the answer to the user asking the question.

The interface 128 is configured to provide an interface for an administrator of the ATLOP relation extraction application 118 to train the encoder 122 and the classifier 124, and adjust model parameters, or is configured to provide an interface for a user to use the ATLOP relation extraction application 118 to obtain an answer for a question, to construct or complete a knowledge graph using documents.

Figure 5:
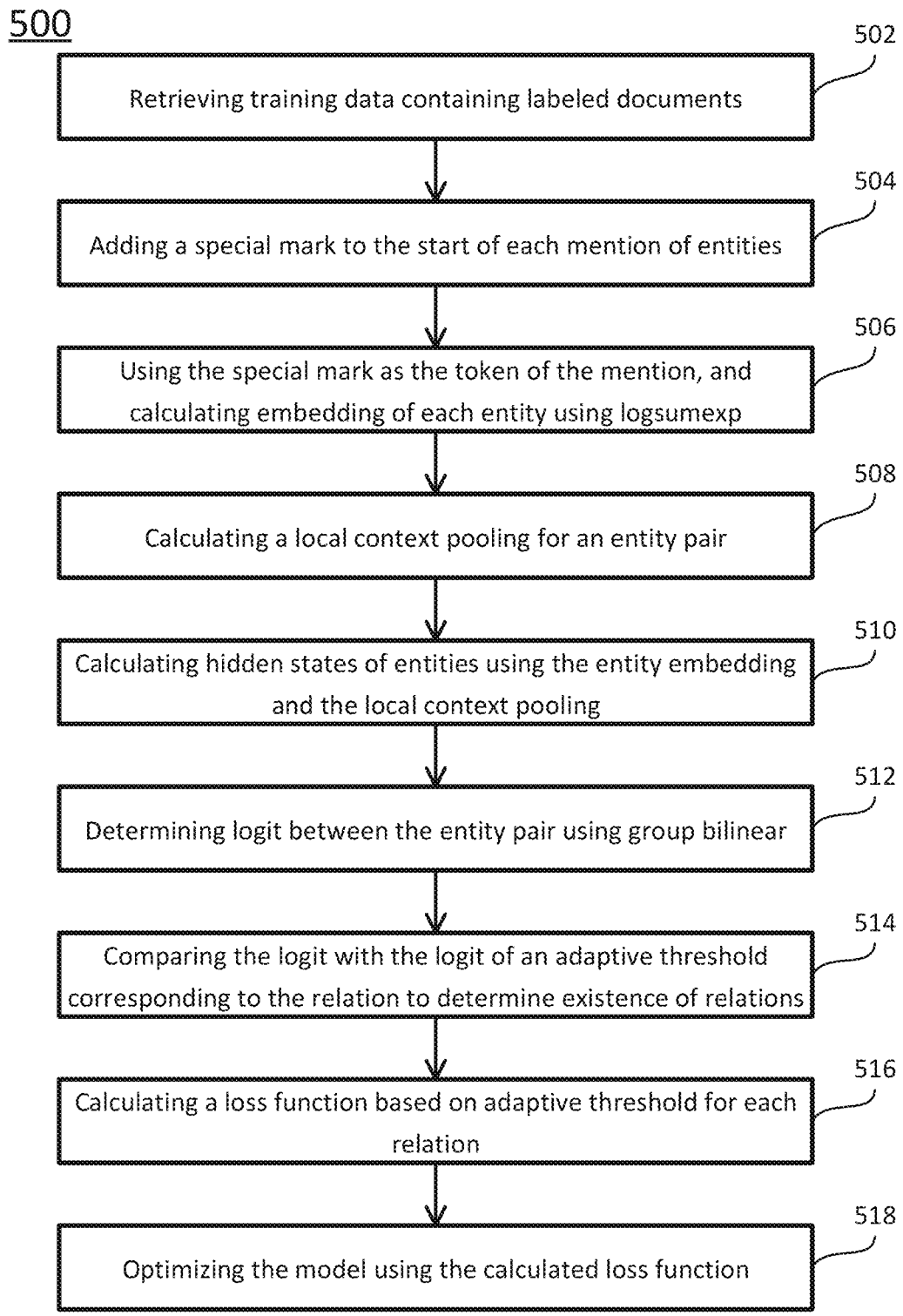
FIG. 5 schematically depicts a training process for the ATLOP relation extraction application according to certain embodiments of the present disclosure.

FIG. 5 schematically depicts a training process for the ATLOP relation extraction application according to certain embodiments of the present disclosure. In certain embodiments, the training process is implemented by the computing device 110 shown in FIG. 1. It should be particularly noted that, unless otherwise stated in the present disclosure, the steps of the training process or method may be arranged in a different sequential order, and are thus not limited to the sequential order as shown in FIG. 5.

As shown in FIG. 5, at procedure 502, the document preparation module 120 retrieves the training data 130, and provides the training data 130 to the encoder 122. The training data are documents with labeled entities and relations.

At procedure 504, for each document, the encoder 122 adds a symbol "*" at start and end of mentions of entities, or in other words, immediately before and after the mentions of the entities.

At procedure 506, the encoder 122 uses the symbol "*" at the start of the mentions as the token representing that mention, calculates an entity embedding using log sum exp, and sends the entity embeddings to the classifier 124. Specifically, the encoder 122 has a basic encoder structure of a language model, such as BERT, and obtains embedding for each token in the training document, that is, $$[h_1, h_2, \ldots, h_l, \ldots, h_l] = \text{BERT}([x_1, x_2, \ldots, x_l, \ldots, x_l]) \quad (1).$$

The embedding for each token is represented by a vector. The encoder 122 then uses the embeddings of the tokens corresponding to the mentions of an entity to obtain the embedding of the entity by log sum exp, that is, $$h_{e_i} = \log \sum_{j=1}^{N_{e_i}} \exp(h_{m_j}). \quad (2)$$

At procedure 508, upon receiving the embeddings of the entities from the encoder 122, the classifier 124 calculates a local context pooling (local context embedding) for an entity pair by:

$$A^{(s,o)} = A_s^E \cdot A_o^E,$$

$$q^{(s,o)} = \sum_{i=1}^{H} A_i^{(s,o)},$$

$$a^{(s,o)} = q^{(s,o)} / 1^T q^{(s,o)},$$

$$c^{(s,o)} = H^T a^{(s,o)}.$$

At procedure 510, the classifier 124 calculates hidden states of the entities using the entity embeddings and the local context pooling. Specifically, for relation prediction of an entity pair containing a subject entity and an object entity, the hidden states of the entities are calculated by:

$$z_s^{(s,o)} = \tanh(W_s h_{e_s} + W_{C1} c^{(s,o)}) \quad (6),$$

$$z_o^{(s,o)} = \tanh(W_o h_{e_o} + W_{C2} c^{(s,o)}) \quad (7).$$

At procedure 512, after obtaining the hidden states of the entities in the entity pair, the classifier 124 determines the logit between the entities using group bilinear:

$$logit_r = \sum_{i=1}^{k} z_s^{iT} W_r^i z_o^i + b_r.$$

At procedure 514, for the logit between the entity pair corresponding to each relation, the classifier 124 compares the determined logit with a logit of an adaptive threshold corresponding to that relation (TH class), and determines that the relation exists if the logit equals to or is greater than the logit function of the threshold, or determines that the relation does not exist if the probability is less than the threshold. Because the documents may include multiple mentions and multiple relations for the entity pair, there may be one or more determined relations for the entity pair.

At procedure 516, the classifier 124 calculates a loss function based on the adaptive threshold using the equations of:

$$L_1 = -\sum_{r \in P_T} \log \left( \frac{\exp(logit_r)}{\sum_{r' \in P_T \cup \{TH\}} \exp(logit_{r'})} \right),$$

-continued $$L_2 = -\log\left(\frac{\exp(logit_{TH})}{\sum_{r' \in N_T \cup \{TH\}} \exp(logit_{r'})}\right),$$

$$L = L_1 + L_2.$$

At procedure 518, the loss function is fed back to the model to adjust parameters of the encoder 122 and the classifier 124, and another round of prediction is performed to optimize the model.

Accordingly, the steps 506-518 are performed iteratively for the same document until the loss L converges at a small value, or until a predetermined rounds of iterations have been reached. Then the steps 502-518 are performed for another document in the training data. In certain embodiments, each round of the training is performed by batch, and each batch includes a number of documents, such as four documents.

Figure 6:
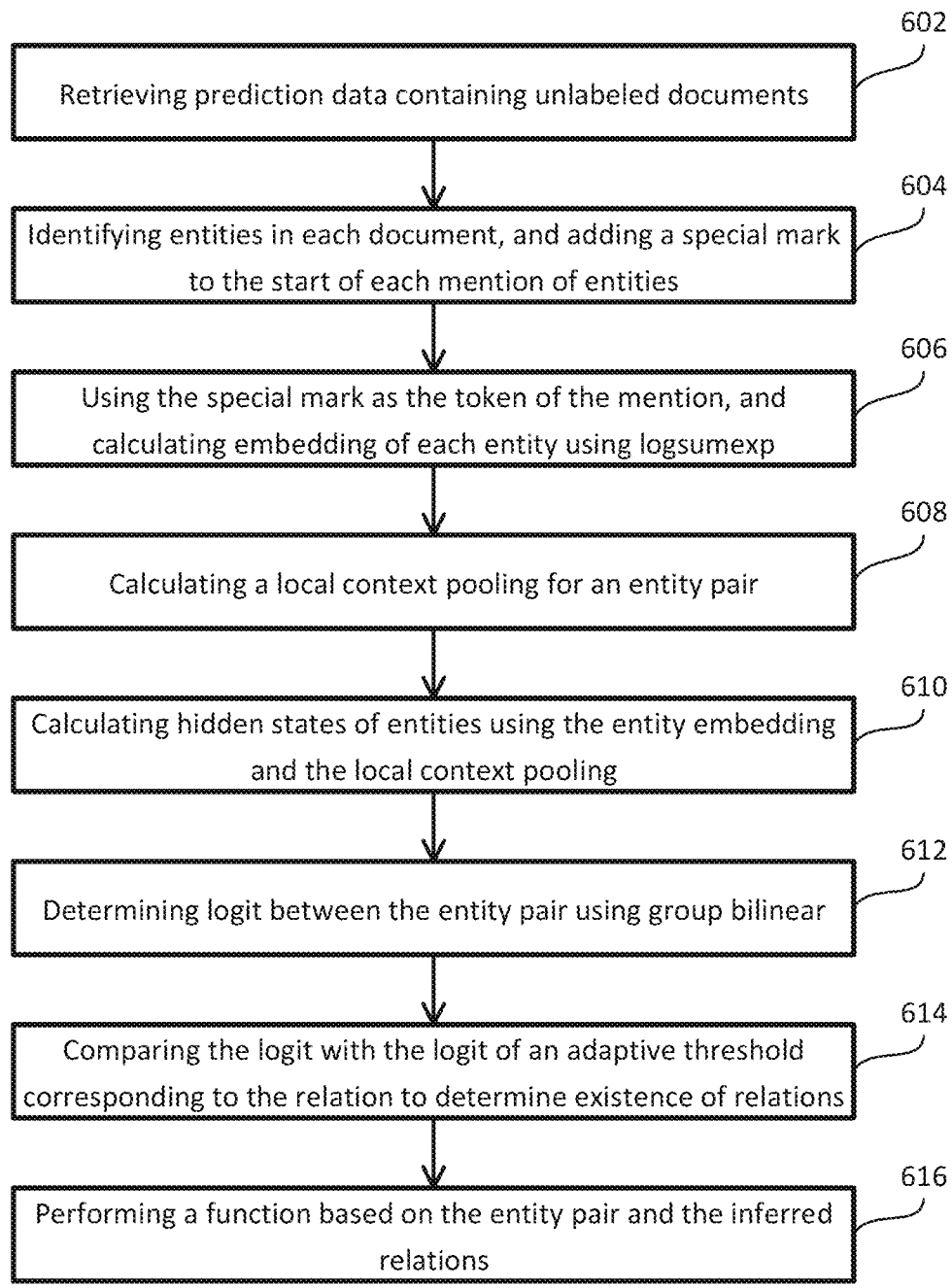
FIG. 6 schematically depicts a inferring process for the ATLOP relation extraction application according to certain embodiments of the present disclosure.

FIG. 6 schematically depicts an inferring process for the ATLOP relation extraction application according to certain embodiments of the present disclosure, after the ATLOP relation extraction application is well-trained. In certain embodiments, the inferring process is implemented by the computing device 110 shown in FIG. 1. It should be particularly noted that, unless otherwise stated in the present disclosure, the steps of the training process or method may be arranged in a different sequential order, and are thus not limited to the sequential order as shown in FIG. 6. Kindly note that the training data of the ATLOP and the document for prediction using ATLOP should be in the same field. For example, a training of the ATLOP using Wikipedia data can be used to infer general knowledge from an article, and a training of the ATLOP using biomedical data can be used to infer gen-disease relations from biomedical papers.

As shown in FIG. 6, at procedure 602, the document preparation module 120 retrieves the prediction data 132, and provides the prediction data 132 to the encoder 122. The prediction data are documents, the entities in the document may or may not be provided, and there is no relation labels.

At procedure 604, for each document, the encoder 122 identifies entities from the document via named-entity recognition such as spaCy or Stanza, and adds a symbol "*" at start and end of mentions of the identified entities in the documents. The list of entities and labels is preferably provided, and thus named-entity recognition is not required.

At procedure 606, the encoder 122 uses the symbol "*" at the start of the mentions as the token representing that mention, calculates an entity embedding using log sum exp, and sends the entity embeddings to the classifier 124. Specifically, the encoder 122 has a basic encoder structure of a language model, such as BERT, and obtains embedding for each token in the training document, that is, $$[h_1, h_2, h_t, \ldots, h_e] = \text{BERT}([x_1, x_2, \ldots, x_t, \ldots, x_l]) \quad (1).$$

The embedding for each token is represented by a vector. The encoder 122 then uses the embeddings of the tokens corresponding to the mentions of an entity to obtain the embedding of the entity by log sum exp, that is, $$h_{e_i} = \log \sum_{j=1}^{N_{e_i}} \exp(h_{m_j}). \quad (2)$$

At procedure 608, upon receiving the embeddings of the entities from the encoder 122, the classifier 124 calculates a local context pooling (local context embedding) for an entity pair by:

$$A^{(s,o)} = A_s^E \cdot A_o^E,$$

$$q^{(s,o)} = \sum_{i=1}^{H} A_i^{(s,o)},$$

$$a^{(s,o)} = q^{(s,o)}/1^T q^{(s,o)},$$

$$c^{(s,o)} = H^T a^{(s,o)}.$$

At procedure 610, the classifier 124 calculates hidden states of the entities using the entity embeddings and the local context pooling. Specifically, for relation prediction of an entity pair containing a subject entity and an object entity, the hidden states of the entities are calculated by:

$$z_s^{(s,o)} = \tanh(W_s h_{e_s} + W_{C1} c^{(s,o)}) \quad (6),$$

$$z_o^{(s,o)} = \tanh(W_o h_{e_o} + W_{C2} c^{(s,o)}) \quad (7).$$

At procedure 612, after obtaining the hidden states of the entities in the entity pair, the classifier 124 determines the logit between the entities using group bilinear:

$$logit_r = \sum_{i=1}^{k} z_s^{iT} W_r^i z_o^i + b_r.$$

At procedure 614, for the logit between the entity pair corresponding to each relation, the classifier 124 compares the determined probability with an adaptive threshold corresponding to that relation (TH class, which is obtained by the training process such as the process shown in FIG. 5) or the logit of the TH ($logit_{TH}$), and determines that the relation exists if the $logit_r$ is greater than the logit function of the threshold $logit_{TH}$, or determines that the relation does not exist if the probability is less than the threshold. Because the documents may include multiple mentions and multiple relations for the entity pair, there may be one or more determined relations for the entity pair. The classifier 124 then sends the entity pairs and the corresponding relations to the function module 126. Therefore, by the inference, the entities in the document and the relations between the entities are obtained.

At procedure 616, upon receiving the entity pairs and the corresponding relations, the function module 126 performs a function. The function may be, for example, constructing or completing a knowledge graph using the entities as nodes and the relations as edges; or providing an answer to a question where the entities are extracted from the question and the entity pair relations are extracted from a database related to the question.

In certain aspects, the present disclosure relates to a non-transitory computer readable medium storing computer executable code. In certain embodiments, the computer executable code may be the software stored in the storage device 116 as described above. The computer executable code, when being executed, may perform one of the methods described above.

EXPERIMENTS

Datasets: Experiments are performed which prove the advantages of certain embodiments of the ATLOP application of the present disclosure. The data set used in the experiments includes DocRED, CDR, and GDA, which are shown in FIG. 7, Table 1. DocRED (Yao et al. 2019) is a large-scale general-purpose dataset for document-level RE constructed from Wikipedia articles. It consists of 3053 human-annotated documents for training. For entity pairs that express relation(s), about 7% of them have more than one relation label. CDR (Li et al. 2016) is a human-annotated dataset in the biomedical domain. It consists of 500 documents for training. The task is to predict the binary interactions between Chemical and Disease concepts. GDA (Wu et al. 2019b) is a large-scale dataset in the biomedical domain. It consists of 29192 articles for training. The task is to predict the binary interactions between Gene and Disease concepts. The experiments follow Christopoulou, Miwa, and Ananiadou (2019) to split the training set into an 80/20 split as training and development sets.

Experiment Settings: The model of the disclosure is implemented based on Pytorch2 and Huggingface's Transformers3. We use cased BERT-base (Devlin et al. 2019) or RoBERTa-large (Liu et al. 2019) as the encoder on DocRED, and cased SciBERT-base (Beltagy, Lo, and Cohan 2019) on CDR and GDA. We use mixed precision training (Micikevicius et al. 2018) based on the Apex library4. Our model is optimized with AdamW (Loshchilov and Hutter 2019) using learning rate $\in\{$2e-5, 3e-5, 5e-5, 1e-4$\}$, with a linear warmup (Goyal et al. 2017) for the first 6% steps followed by a linear decay to 0. All hyper-parameters are tuned on the development set. The hyper-parameters on all datasets are listed in FIG. 8, Table 2.

For models that use a global threshold, we search threshold values from $\{0.1, 0.2, \ldots, 0.9\}$ and pick the one that maximizes dev $F_1$. All models are trained with 1 Tesla V100 GPU. For DocRED dataset, the training takes about 1 hour 45 minutes with BERT-base encoder and 3 hours 30 minutes with RoBERTa-large encoder. For CDR and GDA datasets, the training takes 20 minutes and 3 hours 30 minutes with SciBERT-base encoder, respectively.

Main results: We compare ATLOP with sequence-based models, graph based models, and transformer-based models on the DocRED dataset. The experiment results are shown in FIG. 9, Table 3. Following Yao et al. (2019), we use F1 and Ign F1 in evaluation. The Ign F1 denotes the F1 score excluding the relational facts that are shared by the training and dev/test sets.

Sequence-based Models. These models use neural architectures such as CNN (Goodfellow, Bengio, and Courville 2015) and bidirectional LSTM (Schuster and Paliwal 1997) to encode the entire document, then obtain entity embeddings and predict relations for each entity pair with bilinear function.

Graph-based Models. These models construct document graphs by learning latent graph structures of the document and perform inference with graph convolutional network (Kipf and Welling 2017). We include two state-of-the art graph-based models, AGGCN (Guo, Zhang, and Lu 2019) and LSR (Nan et al. 2020), for comparison. The result of AGGCN is from the re-implementation by Nan et al. (2020).

Transformer-based Models. These models directly adapt pre-trained language models to document-level RE without using graph structures. They can be further divided into pipeline models (BERT-TS (Wang et al. 2019a)), hierarchical models (HIN-BERT (Tang et al. 2020a)), and pre-training methods (CorefBERT and CorefRoBERTa (Ye et al. 2020)). We also include the BERT baseline (Wang et al. 2019a) in our comparison.

We find that our re-implemented BERT baseline gets significantly better results than Wang et al. (2019a), and outperforms the state-of-the-art RNN-based model BiLSTM-LSR by 1.2%. It demonstrates that pre-trained language models can capture long-distance dependencies among entities without explicitly using graph structures. After integrating other techniques, our enhanced baseline BERT-EBASE achieves an F1 score of 58.52%, which is close to the current state-of-the art model BERT-LSRBASE. Our BERT-ATLOPBASE model further improves the performance of BERT-EBASE by 2:6%, demonstrating the efficacy of the proposed two novel techniques. Using RoBERTa-large as the encoder, our ALTOP model achieves an F1 score of 63.40%, which is a new state of-the-art result on DocRED. We held the first position on Colab leaderboard5 as of Sep. 9, 2020.

Results on Biomedical Datasets: Experiment results on two biomedical datasets are shown in FIG. 10, Table 4. Verga, Strubell, and McCallum (2018) and Nguyen and Verspoor (2018) are both sequence-based models that use self-attention network and CNN as the encoders, respectively. Christopoulou, Miwa, and Ananiadou (2019) and Nan et al. (2020) use graph-based models that construct document graphs by heuristics or structured attention, and perform inference with graph neural network. To our best knowledge, transformer-based pre-trained language models have not been applied to document-level RE datasets in the biomedical domain. In experiments, we replace the encoder with $SciBERT_{BASE}$, which is pre-trained on multi-domain corpora of scientific publications. The $SciBERT_{BASE}$ baseline already outperforms all existing methods. Our $SciBERTATLOP_{BASE}$ model further improves the F1 score by 4.3% and 1.4% on CDR and GDA, respectively, and yields the new state-of-the-art results on these two datasets.

Ablation Study: To show the efficacy of our proposed techniques, we conduct two sets of ablation studies on ATLOP and enhanced baseline, by turning off one component at a time. As shown in FIG. 11, Table 5, we observe that all components contribute to model performance. The adaptive thresholding and localized context pooling are equally important to model performance, leading to a drop of 0.89% and 0.97% in dev F1 score respectively when removed from ATLOP. Note that the adaptive thresholding only works when the model is optimized with the adaptive-thresholding loss. Applying adaptive thresholding to models trained with binary cross entropy results in dev F1 of 41.74%.

For our enhanced baseline model BERT-EBASE, both group bilinear and log sum exp pooling lead to about 1% increase in dev F1. We find the improvement from entity markers is minor (0.24% in dev F1) but still use the technique in the model as it makes the derivation of mention embedding and mention-level attention easier.

Analysis of Thresholding: Global thresholding does not consider the variations of model confidence in different classes or instances, and thus yields suboptimal performance. One interesting problem is whether we can improve global thresholding by tuning different thresholds for different classes. Thus, we experiment on tuning class-dependent thresholds to maximize the F1 score on the development set of DocRED using the cyclic optimization algorithm (Fan and Lin 2007). Results are shown in FIG. 12, Table 6. We find that using per-class thresholding significantly improves the dev F1 score to 61.73%, which is even higher than the result of adaptive thresholding. However, this gain does not transfer to the test set. The result of per-class thresholding is even worse than that of global thresholding.

While our adaptive thresholding technique uses a learnable threshold that can automatically generalize to the test set.

Analysis of Context Pooling: To show that our localized context pooling (LOP) technique mitigates the multi-entity issue, we divide the documents in the development set of DocRED into different groups by the number of entities, and evaluate models trained with or without localized context pooling on each group. Experiment results are shown in FIG. 13. We observe that for both models, their performance gets worse when the document contains more entities. The model w/LOP consistently outperforms the model w/o LOP except when the document contains very few entities (1 to 5), and the improvement gets larger when the number of entities increases. However, the number of documents that only contain 1 to 5 entities is very small (4 in the dev set), and the documents in DocRED contain 19 entities on average. Therefore, our localized context pooling still improves the overall F1 score significantly. This indicates that the localized context pooling technique can capture related context for entity pairs and thus alleviates the multi-entity problem.

We also visualize the context weights of the example in FIG. 2. As shown in FIG. 14, our localized context pooling gives high weights to born and died, which are most relevant to both entities (John Stanistreet, Bendigo). These two tokens are also evidence for the two ground truth relationships place of birth and place of death, respectively. Tokens like elected and politician get much smaller weights because they are only related to the subject entity John Stanistreet. The visualization demonstrates that the localized context can locate the context that is related to both entities.

In summary, certain embodiments of the present disclosure provide the ATLOP model for document level relation extraction, which features at least two novel techniques: adaptive thresholding and localized context pooling. The adaptive thresholding technique replaces the global threshold in multi-label classification with a learnable threshold class that can decide the best threshold for each entity pair. The localized context pooling utilizes pre-trained attention heads to locate relevant context for entity pairs and thus helps in alleviating the multi-entity problem. Experiments on three public document-level relation extraction datasets demonstrate that our ATLOP model significantly outperforms existing models and yields the new state-of-the-art results on all datasets.

The ATLOP model has downstream applications to many other NLP tasks, such as knowledge graph construction, information retrieval, question answering and dialogue systems.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

LISTING OF REFERENCES (INCORPORATED HEREIN BY REFERENCE IN THEIR ENTIRETY)

1. Christoph Alt, Marc Hubner, and Leonhard Hennig, Improving relation extraction by pre-trained language representations, 2019, arXiv:1906.03088.
2. Iz Beltagy, Kyle Lo, and Arman Cohan, SciBERT: a pretrained language model for scientific text, 2019, arXiv:1903.10676.
3. Fenia Christopoulou, Makoto Miwa, and Sophia Ananiadou, A walk-based model on entity graphs for relation extraction, 2018, arXiv:1902.07023.
4. Fenia Christopoulou, Makoto Miwa, and Sophia Ananiadou, Connecting the dots: document-level neural relation extraction with edge-oriented graphs, 2019, arXiv:1909.00228.
5. Junyong Chung, Caglar Gulcehre, KyungHyun Cho, and Yoshua Bengio, Empirical evaluation of gated recurrent neural networks on sequence modeling, 2014, arXiv:1412.3555.
6. Kevin Clark, Urvashi Khandelwal, Omer Levy, Christopher D. Manning, What does BERT look at? An analysis of BERT's attention, 2019, arXiv:1906.04341.
7. Jacob Devlin, Ming-Wei Chang, Kenton Lee, Kristina Toutanova, BERT: pre-training of deep bidirectional transformers for language understanding, 2019, arXiv:1810.04805.
8. Rong-En Fan, and Chih-Jen Lin, A study on threshold selection for multi-label classification, 2007, Semantic Scholar.
9. Priya Goyal, Piotr Dollár, Ross Girshick, Pieter Noordhuis, Lukasz Wesolowski, Aapo Kyrola, Andrew Tulloch, Yangqing Jia, Kaiming He, Accurate, large minibatch SGD: training ImageNet in 1 hour, 2017, arXiv:1706.02677.
10. Zhijiang Guo, Yan Zhang, and Wei Lu, Attention guided graph convolutional networks for relation extraction, 2019, Proceedings of the 57th Annual Meeting of the Association for Computational Linguistics, 241-251.
11. Pankaj Gupta, Subburam Rajaram, Hinrich Schütze, Bernt Andrassy, Thomas Runkler, Neural relation extraction within and across sentence boundaries, 2019, arXiv:1810.05102.
12. Iris Hendrickx, Su Nam Kim, Zornitsa Kozareva, Preslav Nakov, Diarmuid Ó Séaghdha, Sebastian Padó, Marco Pennacchiotti, Lorenza Romano, Stan Szpakowicz, SemEval-2010 Task 8: multi-way classification of semantic relations between pairs of nominals, 2010, Proceedings of the 5th International Workshop on Semantic Evaluation, 33-38.
13. John Hewitt, Christopher D. Manning, A structural probe for finding syntax in word representations, NAACL-HLT, 2019, 4129-4138.
14. Sepp Hochreiter and Jurgen Schmidhuber, Long shortterm memory. Neural Computation, 1997, 9(8): 1735-1780.
15. Robin Jia, Cliff Wong, and Hoifung Poon, Documentlevel N-ary relation extraction with multiscale representation learning, 2019, arXiv: 1904.02347.
16. Urvashi Khandelwal, He He, Peng Qi, and Dan Jurafsky, Sharp nearby, fuzzy far away: how neural language models use context, 2018, arXiv: 1805.04623.

17. Thomas N. Kipf and Max Welling, Semi-supervised classification with graph convolutional networks, 2017, arXiv: 1609.02907.
18. Jiao Li, Yueping Sun, Robin J. Johnson, Daniela Sciaky, Chih-Hsuan Wei, Robert Leaman, Allan Peter Davis, Carolyn J. Mattingly, Thomas C. Wiegers, and Zhiyong Lu, BioCreative V CDR task corpus: a resource for chemical disease relation extraction, Database, 2016, 1-10.
19. Yann LeCun, Yoshua Bengio & Geoffrey Hinton, Deep learning, Nature, 2015, 521:436-444.
20. Xiaodan Liang, Xiaohui Shen, Jiashi Feng, Liang Lin, and Shuicheng Yan, Semantic object parsing with graph LSTM, 2016, arXiv: 1603.07063.
21. Yang Liu, and Mirella Lapata, Learning structured text representations, Transactions of the Association for Computational Linguistics, 2018, 6: 63-75.
22. Yinhan Liu, Myle Ott, Naman Goyal, Jingfei Du, Mandar Joshi, Danqi Chen, Omer Levy, Mike Lewis, Luke Zettlemoyer, Veselin Stoyanov, RoBERTa: a robustly optimized BERT pretraining approach, 2019, arXiv: 1907.11692.
23. Ilya Loshchilov, and Frank Hutter, Decoupled weight decay regularization, 2019, ICLR 2019 Conference.
24. Aditya K. Menon, Ankit Singh Rawat, Sashank Reddi, and Sanjiv Kumar, Multilabel reductions: what is my loss optimising? 2019, NeurIPS2019.
25. Paulius Micikevicius, Sharan Narang, Jonah Alben, Gregory Diamos, Erich Elsen, David Garcia, Boris Ginsburg, Michael Houston, Oleksii Kuchaiev, Ganesh Venkatesh, Hao Wu, Mixed precision training, 2018, arXiv: 1710.03740.
26. Makoto Miwa, Mohit Bansal, End-to-End Relation Extraction using LSTMs on sequences and tree structures, 2016, arXiv: 1601.00770.
27. Guoshun Nan, Zhijiang Guo, Ivan Sekulic, Wei Lu, Reasoning with latent structure refinement for document-level relation extraction, 2020, arXiv: 2005.06312.
28. Dat Quoc Nguyen, and Karin Verspoor, Convolutional neural networks for chemical-disease relation extraction are improved with character-based word embeddings, 2018, arXiv: 1805.10586.
29. Nanyun Peng, Hoifung Poon, Chris Quirk, Kristina Toutanova, and Wen-tau Yih, Cross-sentence N-ary relation extraction with graph LSTMs, 2017, arXiv: 1708:03743.
30. Chris Quirk, and Hoifung Poon, Distant supervision for relation extraction beyond the sentence boundary, 2017, arXiv: 1609.04873.
31. Sashank J. Reddi, Satyen Kale, Felix Yu, Dan Holtmann-Rice, Jiecao Chen, and Sanjiv Kumar, Stochastic negative mining for learning with large output spaces, 2019, arXiv: 1810.07076.
32. Mike Schuster, and Kuldip K. Paliwal, Bidirectional recurrent neural networks, IEEE Transactions on Signal Processing, 1997, 45(11): 2673-2681.
33. Peng Shi, and Jimmy Lin, Simple BERT models for relation extraction and semantic role labeling, 2019, arXiv: 1904.05255.
34. Livio Baldini Soares, Nicholas FitzGerald, Jeffrey Ling, and Tom Kwiatkowski, Matching the blanks: distributional similarity for relation learning, 2019, arXiv: 1906.03158.
35. Linfeng Song, Yue Zhang, Zhiguo Wang, and Daniel Gildea, N-ary relation extraction using graph state LSTM, EMNLP, 2018, 2226-2235.
36. Hengzhu Tang, Yanan Cao, Zhenyu Zhang, Jiangxia Cao, Fang Fang, Shi Wang, and Pengfei Yin, HIN: hierarchical inference network for document-level relation extraction, Advances in Knowledge Discovery and Data Mining, 2020, 12084: 197-209.
37. Yun Tang, Jing Huang, Guangtao Wang, Xiaodong He, Bowen Zhou, Orthogonal relation transforms with graph context modeling for knowledge graph embedding, ACL, 2020, 2713-2722.
38. Ian Tenney, Dipanjan Das, and Ellie Pavlick, BERT rediscovers the classical NLP pipeline, ACL, 2019, 4593-4601.
39. Ashish Vaswani, Noam Shazeer, Niki Parmar, Jakob Uszkoreit, Llion Jones, Aidan N. Gomez, Lukasz Kaiser, and Illia Polosukhin, Attention is all you need, 2017, arXiv: 1706.03762.
40. Patrick Verga, Emma Strubell, and Andrew McCallum, Simultaneously self-attending to all mentions for full-abstract biological relation extraction, NAACL-HLT, 2018, 872-884.
41. Jesse Vig, and Yonatan Belinkov, Analyzing the structure of attention in a transformer language model, 2019, arXiv: 1906.04284.
42. Hong Wang, Christfried Focke, Rob Sylvester, Nilesh Mishra, and William Wang, Fine-tune BERT for DocRED with two-step process, 2019, arXiv: 1909.11898.
43. Haoyu Wang, Ming Tan, Mo Yu, Shiyu Chang, Dakuo Wang, Kun Xu, Xiaoxiao Guo, and Saloni Potdar, Extracting multiple-relations in one-pass with pre-trained transformers, 2019, arXiv: 1902.01030.
44. Linlin Wang, Zhu Cao, Gerard de Melo, and Zhiyuan Liu, Relation classification via multi-Level attention CNNs, ACL, 2016, 1298-1307.
45. Felix Wu, Tianyi Zhang, Amauri Holanda de Souza Jr, Christopher Fifty, Tao Yu, Kilian Q Weinberger, Simplifying graph convolutional networks, 2019a, arXiv: 1902.07153.
46. Ye Wu, Ruibang Luo, Henry C. M. Leung, Hing-Fung Ting, and Tak-Wah Lam, RENET: a deep learning approach for extracting gene-disease associations from literature, RECOMB, 2019b, 272-284.
47. Yuan Yao, Deming Ye, Peng Li, Xu Han, Yankai Lin, Zhenghao Liu, Zhiyuan Liu, Lixin Huang, Jie Zhou, and Maosong Sun, DocRED: a large-scale document-level relation extraction dataset, ACL, 2019, 764-777.
48. Deming Ye, Yankai Lin, Jiaju Du, Zhenghao Liu, Peng Li, Maosong Sun, Zhiyuan Liu, Coreferential reasoning learning for language representation, 2020, arXiv: 2004.06870.
49. Daojian Zeng, Kang Liu, Siwei Lai, Guangyou Zhou, and Jun Zhao, Relation classification via convolutional deep neural network, COLING, 2014, 2335-2344.
50. Yuhao Zhang, Peng Qi, and Christopher D. Manning, Graph convolution over pruned dependency trees improves relation extraction, EMNLP, 2018, 2205-2215.
51. Yuhao Zhang, Victor Zhong, Danqi Chen, Gabor Angeli, and Christopher D. Manning, Position-aware attention and supervised data improve slot filling, EMNLP, 2017, 35-45.
52. Zhengyan Zhang, Xu Han, Zhiyuan Liu, Xin Jiang, Maosong Sun, and Qun Liu, ERNIE: enhanced language representation with informative entities, 2019, arXiv: 1905.07129.
53. Heliang Zheng, Jianlong Fu, Zheng-Jun Zha, and Jiebo Luo, Learning deep bilinear transformation for fine-grained image representation, 2019, arXiv: 1911.03621.

What is claimed is:

1. A system comprising a computing device, the computing device comprising a processor and a storage device storing computer executable code, wherein the computer executable code, when executed at the processor, is configured to:

provide a document;

embed a plurality of entities in the document into a plurality of embedding vectors; and predict one of a plurality of relations between a first entity in the document and a second entity in the document based on a first embedding vector and a second embedding vector, the first embedding vector of the plurality of embedding vectors representing the first entity, and the second embedding vector of the plurality of embedding vectors representing the second entity, wherein the computer executable code is configured to embed and predict using a language model stored in the computing device, each of the plurality of relations has an adaptive threshold, and the one of the plurality of relations is determined to exist when a logit of the relation is greater than a logit function of corresponding one of the adaptive thresholds of the relations, wherein the computer executable code is configured to predict one of a plurality of relations by calculating a local context pooling for a pair of entities selected from the plurality of entities using:

$$A^{(s,o)} = A_s^E \cdot A_o^E,$$

$$q^{(s,o)} = \sum_{i=1}^{H} A_i^{(s,o)},$$

$$a^{(s,o)} = q^{(s,o)}/1^T q^{(s,o)}, \text{ and}$$

$$c^{(s,o)} = H^T a^{(s,o)},$$

wherein the pair of entities comprises a subject entity and an object entity, $A_s^E$ is a token-level attention heads of the subject entity, $A_o^E$ is a token-level attention heads of the object entity, $A^{(s,o)}$ is a multiplication of $A_s^E$ and $A_o^E$, H in $$\sum_{i=1}^{H} A_i^{(s,o)}$$

is a number of attention heads, $A_i^{(s,o)}$ is an i-th multiplication of H multiplications, $a^{(s,o)}$ is normalization of $q^{(s,o)}$ to sum 1, H in $H^T a^{(s,o)}$ is last layer embedding of the language model that is pre-trained, and $c^{(s,o)}$ is the local context pooling for the pair of entities.

2. The system of claim 1, wherein the computer executable code is configured to embed each of the plurality of entities by summarizing at least one hidden representation of at least one mention of the entity using LogSumExp (LSE).

3. The system of claim 1, wherein hidden states of the subject entity and the object entity are determined by:

$$z_s^{(s,o)} = \tanh(W_s h_{e_s} + W_{C1} c^{(s,o)}), \text{ and}$$

$$z_o^{(s,o)} = \tanh(W_o h_{e_o} + W_{C2} c^{(s,o)}),$$

wherein $h_{e_s}$ is the embedding of the subject entity, $z_s^{(s,o)}$ is hidden state of the subject entity, $h_{e_o}$ is the embedding of the object entity, $z_o^{(s,o)}$ is hidden state of the object entity, and $W_s$, $W_o$, $W_{C1}$ and $W_{C2}$ are model parameters.

4. The system of claim 3, wherein the computer executable code is configured to predict relation between the subject entity and the object entity using:

$$logit_r = \sum_{i=1}^{k} z_s^{iT} W_r^i z_o^i + b_r,$$

wherein $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, and $W_r^i$ and $b_r$ are model parameters; and wherein when the $logit_r$ is greater than a logit function of a learnable threshold TH of the relation r, the subject entity $e_s$ and the object entity $e_o$ have the relation r.

5. The system of claim 4, wherein the dimensions of the $z_s^{(s,o)}$ and the dimensions of the $z_o^{(s,o)}$ are 768, and k is 12.

6. The system of claim 1, wherein the language model comprises at least one of a bidirectional encoder representations from transformer (BERT), a robustly optimized BERT approach (roBERTa), SciBERT, a generative pre-training model (GPT), a GPT-2, and a reparameterized transformer-XL network (XLnet).

7. The system of claim 6, wherein loss function for training the language model is determined by:

$$logit_r = \sum_{i=1}^{k} z_s^{iT} W_r^i z_o^i + b_r,$$

$$L_1 = -\sum_{r \in P_T} \log\left(\frac{\exp(logit_r)}{\sum_{r' \in P_T \cup \{TH\}} \exp(logit_{r'})}\right),$$

$$L_2 = -\log\left(\frac{\exp(logit_{TH})}{\sum_{r' \in N_T \cup \{TH\}} \exp(logit_{r'})}\right), \text{ and}$$

$$L = L_1 + L_2,$$

wherein $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, $W_r^i$ and $b_r$ are model parameters, TH is a learnable threshold of the relation, $P_T$ represents positive classes of relations, and NT represents negative classes of relations.

8. The system of claim 1, wherein the computer executable code is further configured to: use the first entity, the second entity, and the predicted one of the plurality of relations between the first entity and the second entity to construct a knowledge graph.

9. The system of claim 1, wherein the computer executable code is further configured to, when a question comprises the first entity and the second entity, and the document is predetermined to comprise an answer to the question: use the predicted one of the plurality of relations to form the answer.

10. A method comprising:
providing, by a computing device, a document;
embedding, by a computing device, a plurality of entities in the document into a plurality of embedding vectors; and
predicting, by a computing device, one of a plurality of relations between a first entity in the document and a second entity in the document based on a first embedding vector and a second embedding vector, the first embedding vector of the plurality of embedding vectors representing the first entity, and the second embedding vector of the plurality of embedding vectors representing the second entity,
wherein the steps of embedding and predicting are performed by a language model stored in the computing device, each of the plurality of relations has an adaptive threshold, and the one of the plurality of relations is determined to exist when a logit of the relation is greater than a logit function of corresponding one of the adaptive thresholds of the relations,
wherein the step of predicting comprises calculating a local context pooling for a pair of entities selected from the plurality of entities using:

$A^{(s,o)} = A_s^E \cdot A_o^E$, $q^{(s,o)} = \sum_{i=1}^{H} A_i^{(s,o)}$, $a^{(s,o)} = q^{(s,o)}/1^T q^{(s,o)}$, and $c^{(s,o)} = H^T a^{(s,o)}$, wherein the pair of entities comprises a subject entity and an object entity, $A_s^E$ is a token-level attention heads of the subject entity, $A_o^E$ is a token-level attention heads of the object entity, $A^{(s,o)}$ is a multiplication of $A_s^E$ and $A_o^E$, H in $\Sigma_{i=1}^H A_i^{(s,o)}$ is a number of heads, $A_i^{(s,o)}$ is an i-th multiplication of H multiplications, $a^{(s,o)}$ is normalization of $q^{(s,o)}$ to sum 1, H in $H^T a^{(s,o)}$ is last layer embedding of the language model that is pre-trained, and $c^{(s,o)}$ is the local context pooling for the pair of entities.

11. The method of claim 10, wherein the steps of embedding of each of the plurality of entities is performed by summarizing at least one hidden representation of at least one mention of the entity using LogSumExp (LSE).

12. The method of claim 10, wherein hidden states of the subject entity and the object entity are determined by:

$z_s^{(s,o)} = \tanh(W_s h_{e_s} + W_{C1} c^{(s,o)})$, and $z_o^{(s,o)} = \tanh(W_o h_{e_o} + W_{C2} c^{(s,o)})$, wherein $h_{e_s}$ is the embedding of the subject entity, $z_s^{(s,o)}$ is hidden state of the subject entity, $h_{e_o}$ is the embedding of the object entity, $z_o^{(s,o)}$ is hidden state of the object entity, and $W_s$, $W_o$, $W_{C1}$, and $W_{C2}$ are model parameters.

13. The method of claim 12, wherein the step of predicting relation between the subject entity and the object entity is performed using:

$logit_r = \sum_{i=1}^{k} z_s^{iT} W_r^i z_o^i + b_r$, wherein $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, and $W_r^i$ and $b_r$ are model parameters; and wherein when the $logit_r$ is greater than a logit function of a learnable threshold TH of the relation r, the subject entity $e_s$ and the object entity $e_o$ have the relation r.

14. The method of claim 13, wherein the language model comprises a bidirectional encoder representations from transformer (BERT) or SciBERT, and the loss function for training the language model is determined by:

$logit_r = \sum_{i=1}^{k} z_s^{iT} W_r^i z_o^i + b_r$, $L_1 = -\sum_{r \in P_T} \log\left(\frac{\exp(logit_r)}{\sum_{r' \in P_T \cup \{TH\}} \exp(logit_{r'})}\right)$, $L_2 = -\log\left(\frac{\exp(logit_{TH})}{\sum_{r' \in N_T \cup \{TH\}} \exp(logit_{r'})}\right)$, and $L = L_1 + L_2$, wherein $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, $W_r^i$ and $b_r$ are model parameters, TH is a learnable threshold of the relation, $P_T$ represents positive classes of relations, and NT represents negative classes of relations.

15. The method of claim 10, further comprising:
using the first entity, the second entity, and the predicted one of the plurality of relations between the first entity and the second entity to construct a knowledge graph; or when a question comprises the first entity and the second entity, and the document is predetermined to comprise an answer to the question: using the predicted one of the plurality of relations to form the answer.

16. A non-transitory computer readable medium storing computer executable code, wherein the computer executable code, when executed at a processor of an active computing device, is configured to:
provide a document;
embed a plurality of entities in the document into a plurality of embedding vectors; and
predict one of a plurality of relations between a first entity in the document and a second entity in the document based on a first embedding vector and a second embedding vector, the first embedding vector of the plurality of embedding vectors representing the first entity, and the second embedding vector of the plurality of embedding vectors representing the second entity,
wherein the computer executable code is configured to embed and predict using a language model stored in the non-transitory computer readable medium, each of the plurality of relations has an adaptive threshold, and the one of the plurality of relations is determined to exist when a logit of the relation is greater than a logit function of corresponding one of the adaptive thresholds of the relations, wherein the computer executable code is configured to predict one of a plurality of relations by calculating a local context pooling for a pair of entities selected from the plurality of entities using:

$$A^{(s,o)} = A_s^E \cdot A_o^E,$$

$$q^{(s,o)} = \sum_{i=1}^{H} A_i^{(s,o)},$$

$$a^{(s,o)} = q^{(s,o)}/1^T q^{(s,o)}, \text{ and}$$

$$c^{(s,o)} = H^T a^{(s,o)},$$

wherein the pair of entities comprises a subject entity and an object entity, $A_s^E$ is a token-level attention heads of the subject entity, $A_o^E$ is a token-level attention heads of the object entity, $A^{(s,o)}$ is a multiplication of $A_s^E$ and $A_o^E$, H is a number of heads, $A_i^{(s,o)}$ is an i-th multiplication of H multiplications, $a^{(s,o)}$ is normalization of $q^{(s,o)}$ to sum 1, and $c^{(s,o)}$ is the local context pooling for the pair of entities.

17. The non-transitory computer readable medium of claim 16,
wherein hidden states of the subject entity and the object entity are determined by:

$$z_s^{(s,o)} = \tanh(W_s h_{e_s} + W_{C1} c^{(s,o)}), \text{ and}$$

$$z_o^{(s,o)} = \tanh(W_o h_{e_o} + W_{C2} c^{(s,o)}),$$

wherein $h_{e_s}$ is the embedding of the subject entity, $z_s^{(s,o)}$ is hidden state of the subject entity, $h_{e_o}$ is the embedding of the object entity, $z_o^{(s,o)}$ is hidden state of the object entity, and $W_s$, $W_o$, $W_{C1}$, and $W_{C2}$ are model parameters; and
wherein the computer executable code is configured to predict relation between the subject entity and the object entity using:

$$logit_r = \sum_{i=1}^{k} z_s^{iT} W_r^i z_o^i + b_r,$$

wherein $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, $W_r^i$ and $b_r$ are model parameters, and when the $logit_r$ is greater than a logit function of a learnable threshold TH of the relation r, the subject entity $e_s$ and the object entity $e_o$ have the relation r.

18. The non-transitory computer readable medium of claim 16, wherein the language model comprises a bidirectional encoder representations from transformer (BERT), and the loss function for training the language model is determined by:

$$logit_r = \sum_{i=1}^{k} z_s^{iT} W_r^i z_o^i + b_r,$$

$$L_1 = -\sum_{r \in P_T} \log\left(\frac{\exp(logit_r)}{\sum_{r' \in P_T \cup \{TH\}} \exp(logit_{r'})}\right),$$

$$L_2 = -\log\left(\frac{\exp(logit_{TH})}{\sum_{r' \in N_T \cup \{TH\}} \exp(logit_{r'})}\right), \text{ and}$$

$$L = L_1 + L_2,$$

wherein $logit_r$ is logit function of the subject entity $e_s$ and the object entity $e_o$ in regard to the relation r, k is a positive integer, dimensions of the $z_s^{(s,o)}$ are divided by k to form a plurality of $z_s^i$, dimension of the $z_o^{(s,o)}$ are divided by k to form a plurality of $z_o^i$, $W_r^i$ and $b_r$ are model parameters, TH is a learnable threshold of the relation, $P_T$ represents positive classes of relations, and NT represents negative classes of relations.

* * * * *